United States Patent
Le Vezouet et al.

(10) Patent No.: US 8,937,177 B2
(45) Date of Patent: Jan. 20, 2015

(54) PYRIDAZINE COMPOUNDS FOR CONTROLLING INVERTEBRATE PESTS

(75) Inventors: Ronan Le Vezouet, Mannheim (DE); Sebastian Soergel, Ludwigshafen (DE); Christian Defieber, Mannheim (DE); Steffen Gross, Ludwigshafen (DE); Karsten Koerber, Eppelheim (DE); Douglas D. Anspaugh, Apex, NC (US); Deborah L. Culbertson, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/636,387

(22) PCT Filed: Mar. 22, 2011

(86) PCT No.: PCT/IB2011/051186
§ 371 (c)(1),
(2), (4) Date: Sep. 21, 2012

(87) PCT Pub. No.: WO2011/117806
PCT Pub. Date: Sep. 29, 2011

(65) Prior Publication Data
US 2013/0012382 A1 Jan. 10, 2013

Related U.S. Application Data

(60) Provisional application No. 61/316,500, filed on Mar. 23, 2010.

(51) Int. Cl.
| | | |
|---|---|---|
| A01N 43/647 | (2006.01) | |
| C07D 403/12 | (2006.01) | |
| A01P 7/00 | (2006.01) | |
| C07D 231/40 | (2006.01) | |
| C07D 253/06 | (2006.01) | |

(52) U.S. Cl.
CPC ............ C07D 231/40 (2013.01); C07D 253/06 (2013.01); C07D 403/12 (2013.01)
USPC ........................ 544/238; 504/100; 514/252.05

(58) Field of Classification Search
CPC ... C07D 231/40; C07D 253/06; C07D 403/12
USPC ........................ 544/238; 504/100; 514/252.05
See application file for complete search history.

(56) References Cited

U.S. PATENT DOCUMENTS

| | | |
|---|---|---|
| 2007/0203148 A1 | 8/2007 | Dunkel et al. |
| 2008/0058389 A1 | 3/2008 | Dunkel et al. |
| 2009/0163516 A1 | 6/2009 | Dunkel et al. |
| 2009/0176844 A1 | 7/2009 | Dunkel et al. |
| 2009/0247586 A1 | 10/2009 | Dunkel et al. |

FOREIGN PATENT DOCUMENTS

| | | |
|---|---|---|
| WO | WO 2004/106324 | 12/2004 |
| WO | WO 2004106324 A1 * | 12/2004 |
| WO | WO 2005/040152 | 5/2005 |
| WO | WO 2005040152 A1 * | 5/2005 |
| WO | WO 2005/074686 | 8/2005 |
| WO | WO 2005/075411 | 8/2005 |
| WO | WO 2007/068373 | 6/2007 |
| WO | WO 2007/068375 | 6/2007 |
| WO | WO 2007/068377 | 6/2007 |
| WO | WO 2008/000438 | 1/2008 |
| WO | WO 2010/034737 | 4/2010 |
| WO | WO 2010/034738 | 4/2010 |
| WO | WO 2011/003793 | 1/2011 |
| WO | WO 2011/003796 | 1/2011 |

(Continued)

OTHER PUBLICATIONS

PCT/IB2011/051186, International Search Report, completed Nov. 23, 2011.
PCT/IB2011/051186, International Preliminary Report on Patentability, issued Sep. 25, 2012.
PCT/EP2011/054284, International Search Report, completed May 23, 2011.
PCT/EP2011/054284, International Preliminary Report on Patentability, issued Sep. 25, 2012.

*Primary Examiner* — Janet Epps-Smith
*Assistant Examiner* — Courtney Brown
(74) *Attorney, Agent, or Firm* — Brinks Gilson & Lione

(57) ABSTRACT

The present invention relates to pyridazine compounds of formulae I or II and the salts and N-oxides thereof,

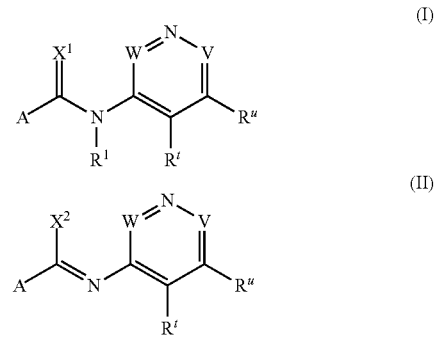

wherein the substituents are as defined in the description, a method for controlling invertebrate pests, to a method for protecting plant propagation material and/or the plants which grow therefrom, to plant propagation material, comprising at least one compound according to the present invention, to a method for treating or protecting an animal from infestation or infection by parasites and to an agricultural composition containing at least one compound according to the present invention.

19 Claims, No Drawings

(56) References Cited

FOREIGN PATENT DOCUMENTS

| WO | WO 2011/009804 | 1/2011 |
| WO | WO 2011/057942 | 5/2011 |
| WO | WO 2011/064188 | 6/2011 |
| WO | WO 2011/117198 | 9/2011 |
| WO | WO 2011/117286 | 9/2011 |

* cited by examiner

PYRIDAZINE COMPOUNDS FOR CONTROLLING INVERTEBRATE PESTS

This application is a National Stage application of International Application No. PCT/IB2011/051186, filed Mar. 22, 2011, which claims the benefit of U.S. Provisional Application No. 61/316,500, filed Mar. 23, 2010, the entire contents of which are hereby incorporated herein by reference.

The present invention relates to novel pyridazine compounds or the enantiomers or veterinarily acceptable salts thereof which are useful for combating or controlling invertebrate pests, in particular arthropod pests and nematodes. The invention further relates to methods for controlling invertebrate pests by using these compounds. The invention further relates to a method for protecting plant propagation material and/or the plants which grow therefrom by using these compounds. The present invention further relates to plant propagation material and to an agricultural and/or veterinary compositions comprising said compounds.

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

WO 2007/068373, WO 2007/068375 and WO 2007/068377 describe derivatives of N-aryl- and N-hetarylamides, derived from carboxylic acids comprising a 5- or 6-membered carbocycle or heterocycle. These compounds are mentioned to be useful for controlling micro-organisms. WO 2005/074686 and WO 2005/075411 describe derivatives of N-arylamides which are mentioned to be useful in control of micro-organismus such as fungi, bacteria in the phyto-protection. WO 2004/035545, WO 2005/040152, WO 2004/106324 and WO 2004/018438 describe triazolcarboxamides derivatives and their use in herbicide field is mentioned. WO 2008/074427 and WO 2008/000438 describe heteroarylcarboxamide derivatives which are mentioned as insecticides. WO 2008/130021 describes pyrazolcarboxamide derivatives and their use as insecticide is mentioned. EP-A 647 635 describes oxadiazole-carboxamides derivatives and their use as herbicides is mentioned.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by compounds of the formulae I and II, as defined below, by their steroisomers and by their salts and N-oxides, in particular their agriculturally or veterinarily acceptable salts.

Therefore, in a first aspect the present invention relates to pyridazines of formulae I or II,

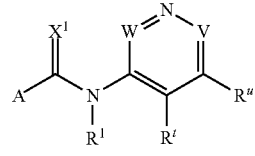
(I)

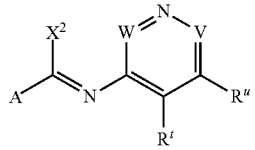
(II)

wherein
A is a triazole or thiadiazole or oxadiazole radical of formulae A1, A2, A3, A4, A5 or A6

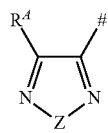
A1

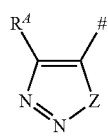
A2

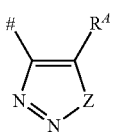
A3

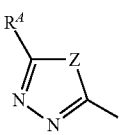
A4

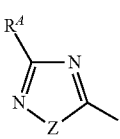
A5

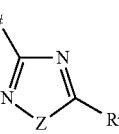
A6 wherein
# denotes the binding site to the remainder of formulae I or II, and wherein
$R^A$ is independently of each other selected from hydrogen, halogen, CN, $NO_2$, $C_1$-$C_{10}$-alkyl, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein each $R^A$ is further independently of each other selected from $OR^a$, $C(Y)R^b$, $C(Y)OR^c$, $S(O)_mR^d$, $NR^eR^f$, heterocyclyl, $C_3$-$C_{10}$-cycloalkyl and $C_5$-$C_{10}$-cycloalkenyl, wherein the last three mentioned radicals may be unsubstituted or may carry 1, 2, 3, 4 or 5 identical or different substituents $R^x$, wherein Z is O, S or $NR^N$
V is $C(R^v)$ or N;
W is $C(R^w)$ or N;
with the proviso that either V or W is N;

$R^N$ is selected from hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from $OR^a$, $C(Y)R^b$, $C(Y)OR^c$, $S(O)_m R^d$, $NR^eR^f$, $C(Y)NR^gR^h$, $S(O)_m NR^eR^f$, $C(Y)NR^1NR^eR^f$, $C_1$-$C_5$-alkylen-$OR^a$, $C_1$-$C_5$-alkylen-CN, $C_1$-$C_5$-alkylen-$C(Y)R^b$, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_m R^d$, $C_1$-$C_5$-alkylen-$S(O)_m NR^eR^f$, $C_1$-$C_5$-alkylen $NR^1NR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents $R^y$ $R^t$, $R^u$, $R^v$ and $R^w$ are independently of each other selected from hydrogen, halogen, $C_1$-$C_3$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$X^1$ is S, O or $NR^{1a}$, wherein $R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, heterocyclyl, phenyl-$C_1$-$C_4$-alkyl, hetaryl-$C_1$-$C_4$-alkyl, heterocyclyl-$C_1$-$C_4$-alkyl wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^2$ is $OR^{2a}$, $NR^{2b}R^{2c}$, $S(O)_m R^{2d}$, wherein $R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2b}$, $R^{2c}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2d}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^1$ is hydrogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $OR^a$, $C(Y)R^b$, $C(Y)OR^c$, $S(O)_2R^d$, $NR^eR^f$, $C(Y)NR^gR^h$, $S(O)_m NR^eR^f$, $C(Y)NR^1NR^eR^f$, phenyl, hetaryl, heterocyclyl, $C_1$-$C_5$-alkylen-$OR^a$, $C_1$-$C_5$-alkylen-CN, phenyl-$C_1$-$C_5$-alkyl, hetaryl-$C_1$-$C_5$-alkyl, heterocyclyl-$C_1$-$C_5$-alkyl, $C_3$-$C_{10}$-cycloalkyl-$C_1$-$C_5$-alkyl, $C_1$-$C_5$-alkylen-$C(Y)R^b$, —$C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_2R^d$, $C_1$-$C_5$-alkylen-$S(O)_m NR^eR^d$, $C_1$-$C_5$-alkylen-$C(Y)NR^1NR^eR^f$ wherein the last sixteen mentioned radicals may be unsubstituted or may carry 1, 2, 3, 4 or 5 identical or different substituents $R^x$ or $R^y$;

m is 0, 1 or 2
Y is O or S;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$- alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^1$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$ alkyl, $C_1$-$C_4$-haloalkyl, $C_1$-$C_4$-alkoxy and $C_1$-$C_4$-haloalkoxy;

$R^x$ are independently of each other selected from cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals $R^y$; and wherein $R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

or their agriculturally or veterinally acceptable salts, N-oxides, enantiomers or diastereomers thereof.

A further aspect of the present invention relates to a method for controlling invertebrate pests which method comprises treating the pests, their food supply, their habitat or their breeding ground or a cultivated plant, plant propagation materials such as seed, soil, area, material or environment in which the pests are growing or may grow, or the materials, plants, seeds, soils, surfaces or spaces to be protected from pest attack or infestation with a pesticidally effective amount of a pyridazine compound of formulae I or II according to the present invention or a salt or an N-oxide thereof.

A further aspect of the present invention relates to a method for protecting plant propagation material, in particular seed, comprising at least one compound of formulae I or II and/or the plants which grow therefrom, which method comprises treating the plant propagation material with a pesticidally effective amount of a pyridazine compound of the formulae I or II according to the present invention or an agriculturally acceptable salt or an N-oxide thereof.

A further aspect of the present invention relates to plant propagation material, comprising at least one compound of formulae I or II according to the present invention and/or an agriculturally acceptable salt or an N-oxide thereof.

A further aspect of the present invention relates to a method for treating or protecting an animal from infestation or infection by parasites especially ectoparasites which comprises bringing the animal in contact with a parasiticidally effective amount of a compound of the formulae I or II according to the present invention or a veterinarily acceptable salt or an N-oxide thereof. Bringing the animal in contact with the compound I or II, its salt or the veterinary composition of the invention means applying or administering it to the animal.

A further aspect of the present invention relates to a method for manufacturing a veterinarily acceptable salt intented for therapeutic application on and/or in animals infested by parasites, characterized in that a compound of the formulae I or II or an agriculturally acceptable salt or an N-oxide thereof according to the present invention is used.

A further aspect of the present invention relates to an agricultural composition containing at least one compound of formulae I or II according to the present invention and/or an agriculturally acceptable salt or an N-oxide thereof and at least one liquid or solid carrier.

Depending on the substitution pattern, the compounds of the formulae I or II may have one or more centers of chirality, in which case they are present as mixtures of enantiomers or diastereomers. The invention provides both the pure enantiomers or diastereomers and their mixtures and the use according to the invention of the pure enantiomers or diastereomers of the compound I or its mixtures. Suitable compounds of the formulae I or II also include all possible geometrical stereoisomers (cis/trans isomers) and mixtures thereof. cis/trans isomers may be present with respect to e.g. an imine group.

The compounds of formulae I or II may be amorphous or may exist in one or more different crystalline states (polymorphs) which may have different macroscopic properties such as stability or show different biological properties such as activities. The present invention includes both amorphous and crystalline compounds of formulae I or II, mixtures of different crystalline states of the respective compound I or II, as well as amorphous or crystalline salts thereof.

Salts of the compounds of the formulae I or II are preferably agriculturally and veterinarily acceptable salts. They can be formed in a customary method, e.g. by reacting the compound with an acid if the compound of formulae I or II has a basic functionality or by reacting the compound with a suitable base if the compound of formula I or II has an acidic functionality.

Suitable agriculturally acceptable salts are especially the salts of those cations or the acid addition salts of those acids whose cations and anions, respectively, do not have any adverse effect on the pesticidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzltriethylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formulae I and II with an acid of the corresponding anion, preferably of hydrochloric acid, hydrobromic acid, sulfuric acid, phosphoric acid or nitric acid.

Veterinarily acceptable salts of the compounds of formulae I and II encompass especially the acid addition salts which are known and accepted in the art for the formation of salts for veterinary use. Suitable acid addition salts, e.g. formed by compounds of formulae I or II containing a basic nitrogen atom, e.g. an amino group, include salts with inorganic acids, for example hydrochlorids, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "N-oxide" includes any compound of formulae I or II which has at least one tertiary nitrogen atom that is oxidized to an N-oxide moiety.

The term "invertebrate pest" as used herein encompasses animal populations, such as insects, arachnids and nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 Jul.-Aug. 17(4):720-8, Protein Eng Des Sel. 2004 January; 17(1):57-66, Nat. Protoc. 2007; 2(5):1225-35, Curr. Opin. Chem. Biol. 2006 Oct. 10(5):487-91. Epub 2006 Aug. 28, Biomaterials. 2001 March; 22(5):405-17, Bioconjug. Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as delta-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073.

The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato Solanum bulbocastanum) or T4-lysozym (e.g. potato cultivars capable of synthesizing these proteins with increased resistance against bacteria such as *Erwinia amylvora*).

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_x$-$C_y$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethyl pentyl, 3-ethylpentyl, 1-propylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "$C_1$-$C_{10}$-haloalkyl" as used herein, which is also expressed as "$C_1$-$C_{10}$-alkyl which may be substituted by halogen", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl. "Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_6$-alkenyl" as used herein and in the alkenyl moiety of alkenyloxy and the like refers to monounsaturated straight-chain or branched hydrocarbon radicals having 2 to 4 ("$C_2$-$C_4$-alkenyl") or 2 to 6 ("$C_2$-$C_6$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like and the positional isomers thereof.

The term "$C_2$-$C_6$-haloalkenyl" as used herein, which is also expressed as "$C_2$-$C_6$-alkenyl which may be substituted by halogen", and the haloalkenyl moieties in haloalkenyloxy, haloalkenylcarbony) and the like refers to unsaturated straight-chain or branched hydrocarbon radicals having 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes in each case a singly unsaturated hydrocarbon radical having usually 2 to 10, preferably 2 to 4 carbon atoms, e.g. ethynyl, propargyl(2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "$C_2$-$C_6$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl") or 2 to 10 ("$C_2$-$C_{10}$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_6$-haloalkynyl" as used herein, which is also expressed as "$C_2$-$C_6$-alkynyl which may be substituted by halogen", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-alkoxy is methoxy or ethoxy. $C_1$-$C_4$-alkoxy is additionally, for example, n-propoxy, 1-methylethoxy(isopropoxy), butoxy, 1-methylpropoxy (sec-butoxy), 2-methylpropoxy (isobutoxy) or 1,1-dimethylethoxy (tert-butoxy). $C_1$-$C_6$-alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-di methylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "cycloalkyl" as used herein and in the cycloalkyl moieties of cycloalkoxy and cycloalkylmethyl denotes in each case a mono- or bicyclic cycloaliphatic radical having usually from 3 to 10 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "$C_n$-$C_m$-cycloalkenyl" as used herein and in the like refers to monounsaturated straight-chain or branched hydrocarbon radicals having n to m (e.g. 2 to 4 "$C_2$-$C_4$-alkenyl" or 2 to 6 ("$C_2$-$C_6$-alkenyl") carbon atoms and a double bond in any position.

The term "halocycloalkyl" as used herein and in the halocycloalkyl moieties of halocycloalkylmethyl denotes in each case a mono- or bicyclic cycloaliphatic radical having usually from 3 to 10 carbon atoms or 3 to 6 carbon atoms, wherein at least one, e.g. 1, 2, 3, 4 or 5 of the hydrogen atoms are replaced by halogen, in particular by fluorine, chlorine or bromine. Examples are 1- and 2-fluorocyclopropyl, 1,2-, 2,2- and 2,3-difluorocyclopropyl, 1,2,2-trifluorocyclopropyl, 2,2,3,3-tetrafluorocyclopropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "$C_3$-$C_6$-cycloalkyl-$C_1$-$C_3$-alkyl" refers to a $C_3$-$C_6$-cycloalkyl group as defined above which is bound to the remainder of the molecule via a $C_1$-$C_3$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_n$-$C_m$-cycloalkyl-$C_o$-$C_p$-alkyl" or "cycloalkylalkyl" as used herein and in the like refer to a cycloalkyl group as defined above having n to m carbon atoms, which is bound to the remainder of the molecule via an alkyl group as defined above having o to p carbon atoms.

The term "$C_n$-$C_m$-cycloalkenyl" as used herein and in the like refers to monounsaturated straight-chain or branched hydrocarbon radicals having n to m (e.g. 2 to 4 "$C_2$-$C_4$-alkenyl" or 2 to 6 ("$C_2$-$C_6$-alkenyl") carbon atoms and a double bond in any position.

The term "halocycloalkyl" as used herein and in the halocycloalkyl moieties of halocycloalkylmethyl denotes in each case a mono- or bicyclic cycloaliphatic radical having usually from 3 to 10 carbon atoms or 3 to 6 carbon atoms, wherein at least one, e.g. 1, 2, 3, 4 or 5 of the hydrogen atoms are replaced by halogen, in particular by fluorine, chlorine or bromine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "$C_3$-$C_6$-cycloalkyl-$C_1$-$C_3$-alkyl" refers to a $C_3$-$C_6$-cycloalkyl group as defined above which is bound to the remainder of the molecule via a $C_1$-$C_3$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "$C_n$-$C_m$-cycloalkyl-$C_o$-$C_p$-alkyl" or "cycloalkylalkyl" as used herein and in the like refer to a cycloalkyl group as defined above having n to m carbon atoms, which is bound to the remainder of the molecule via an alkyl group as defined above having o to p carbon atoms.

The term "alkoxyalkyl" as used herein refers to alkyl usually comprising 1 to 4 carbon atoms, wherein 1 carbon atom carries an alkoxy radical usually comprising 1 to 10, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)butyl, 4-(1-methylpropoxy)-butyl, 4-(2-methylpropoxy)-butyl, 4-(1,1-dimethylethoxy)-butyl and the like.

The term "alkylcarbonyl" (alkyl-C(=O)—), as used herein refers to a straight-chain or branched saturated alkyl group as define above comprising 1 to 10 carbon atoms (=$C_1$-$C_{10}$-alkylcarbonyl), preferably 1 to 4 carbon atoms (=$C_1$-$C_4$-alkylcarbonyl) attached through the carbon atom of the carbonnyl group at any position in the alkyl group.

The term "haloalkylcarbonyl" as used herein refers to an alkylcarbonyl group as defined above wherein the hydrogen atoms are partially or fully substituted by fluorine, chlorine, bromine and/or iodine.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. $C_1$-$C_2$-alkylthio is methylthio or ethylthio. $C_1$-$C_4$-alkylthio is additionally, for example, n-propylthio, 1-methylethylthio (isopropylthio), butylthio, 1-methylpropylthio(sec-butylthio), 2-methylpropylthio(isobutylthio) or 1,1-dimethylethylthio(tert-butylthio). $C_1$-$C_6$-alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. $C_1$-$C_2$-haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl(isobutylsulfinyl) or 1,1-dimethylethylsulfinyl(tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. $C_1$-$C_2$-Haloalkylsulfinyl is, for example, S(O)CH$_2$F, S(O)CHF$_2$, S(O)CF$_3$, S(O)CH$_2$Cl, S(O)CHCl$_2$, S(O)CCl$_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or S(O)C$_2$F$_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, S(O)CH$_2$—C$_2$F$_5$, S(O)CF$_2$—C$_2$F$_5$, 1-(CH$_2$F)-2-fluoroethylsulfinyl, 1-(CH$_2$Cl)-2-chloroethylsulfinyl, 1-(CH$_2$Br)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. $C_1$-$C_2$-alkylsulfonyl is methylsulfonyl or ethylsulfonyl. $C_1$-$C_4$-Alkylsulfonyl is additionally, for example, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl) or 1,1-dimethylethylsulfonyl(tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_6$-haloalkylsulfonyl" is a $C_1$-$C_6$-haloalkyl group, as defined above, attached via a sulfonyl [S(O)$_2$] group. $C_1$-$C_2$-Haloalkylsulfonyl is, for example, S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl, 1-(CH$_2$Br)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "heterocyclyl" includes in general 5-, 6-, 7- or 8-membered monocyclic heterocyclic radicals and 8 to 10 membered bicyclic heterocyclic radicals, the mono- and bicyclic radicals may be saturated, partially unsaturated or unsaturated. The mono- and bicyclic heterocyclic radicals usually comprise 1, 2, 3 or 4 heteroatoms selected from N, O and S as ring members.

Examples of saturated or unsaturated 5- or 6-membered heterocyclic radicals comprise saturated or unsaturated, non-aromatic heterocyclic rings, such as pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, pyrazolidinyl, dihydropyranyl, tetrahydropyranyl, 1,3- and 1,4-dioxanyl, thiopyranyl, dihydrothiopyranyl, tetrahydrothiopyranyl, morpholinyl, thiazinyl and the like. Examples for heterocyclic ring also comprising 1 or 2 carbonyl groups as ring members comprise pyrrolidin-2-only, pyrrolidin-2,5-dionyl, imidazolidin-2-only, oxazolidin-2-only, thiazolidin-2-only and the like.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

The term "hetaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "phenylalkyl" and "phenoxyalkyl" refers to phenyl or phenoxy, respectively, which are bound via an alkyl group, in particular a methyl group (=hetarylmethyl), to the remainder of the molecule, examples including benzyl, 1-phenylethyl, 2-phenylethyl, 2-phenoxyethyl and the like.

The terms "heterocyclylalkyl" and "hetarylalkyl" refers to heterocyclyl or hetaryl, respectively, as defined above which are bound via an alkyl group, in particular a methyl group (=heterocyclylmethyl or hetarylmethyl, respectively), to the remainder of the molecule.

Following notation for a substituent group are defined as follows when used in the text:
Me=methyl, Et=ethyl, Pr=propyl, i-Pr=isopropyl, Bu=n-butyl, i-Bu=isobutyl, s-Bu=secbutyl, t-Bu=tert-butyl, c-Pr=cyclopropyl, Pen=pentyl, c-Pen=cyclopentyl, c-Hex=cyclohexyl, Ac=acetyl, Ph=phenyl.

In addition and if present, the undermentioned notation denotes for example the said meaning of each: 5-$CF_3$ is a trifluoromethyl substituent at position 5; 3-Cl-5-$CF_3$ is a chlorine atom at position 3 and a trifluoromethyl substituent at position 5; 2,6-$(Cl)_2$ is a chlorine atom substituent at positions 2 and 6.

The remarks made below as to preferred embodiments of the variables (substituents) of the compounds of formulae I or II are valid on their own as well as preferably in combination with each other.

The remarks made below concerning preferred embodiments of the variables further are valid concerning the compounds of formulae I or II as well as concerning the uses and methods according to the invention and the composition according to the present invention.

A first preferred embodiment of the invention relates to the pyridazine compounds of the formula I, to their salts and to their N-oxides and to the methods and uses of such compounds.

Among the compounds of the formula I, preference is given to those compounds, wherein $X^1$ is oxygen. These compounds are hereinafter also referred to as compounds of formula I1.

Among the compounds of the formula I, preference is further given to those compounds, wherein $R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $C_1$-$C_4$-alkylene-CN, $OR^a$, $C(Y)R^b$, $C(Y)OR^c$ or $S(O)_2R^d$.

More preferably $R^1$ is hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1$-$C_5$-alkyl, $C_1$-$C_5$-alkylen-$OR^a$, $C_3$-$C_{10}$-cycloalkyl-$C_1$-$C_5$-alkyl.

Another embodiment of the invention relates to pyridazine compounds of the formula II, to the salts and N-oxides thereof and to the methods and uses of such compounds. In the compounds of the formula II, preference is given to those compounds, wherein $X^2$ in formula II is $OR^{2a}$ or $SR^{2a}$. In these compounds $R^{2a}$ is preferably $C_1$-$C_6$-alkyl, $C_3$-$C_6$-alkenyl, $C_3$-$C_6$-alkynyl, $C_3$-$C_6$-cycloalkylmethyl or $C_1$-$C_4$-alkoxy-$C_1$-$C_{10}$-alkyl.

Another embodiment of the invention relates to compounds of the formula II, wherein $X^2$ is $NR^{2b}R^{2c}$. In these compounds $R^{2b}$ and $R^c$ are preferably selected, independently of each other, from $C_1$-$C_6$-alkyl, $C_3$-$C_6$-cycloalkylmethyl or $C_1$-$C_4$-alkoxy-$C_1$-$C_{10}$-alkyl or $R^{2b}$ and $R^{2c}$, together with the nitrogen atom to which they are attached, form a saturated, nitrogen-bound 5- or 6-membered heterocycle which may comprise a further heteroatom selected from O, S and N, e.g. $NR^{2b}R^{2c}$ being 1-pyrrolidinyl, 1-piperidinyl, 1-piperazinyl, 4-morpholinyl or 4-thiomorpholinyl.

Among the compounds of formulae I and II preference is given to those compounds, wherein $R^u$ is selected from hydrogen, halogen, $C_1$-$C_4$-alkyl, $C_1$-$C_3$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl.

Among the compounds of formulae I and II preference is given to those compounds, wherein $R^t$ is selected from hydrogen, halogen, $C_1$-$C_4$-alkyl, $C_1$-$C_3$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl.

Among the compounds of formulae I and II preference is further given to those compounds, wherein W is a group $C(R^w)$. Examples of such compounds are compounds of formulae I or II, wherein the heterocycle comprising the groups V and W is pyridazine-4-yl.

Among the compounds of formulae I and II preference is further given to those compounds selected from 4-pyridazine substituted compounds of formulae I.A or II.A

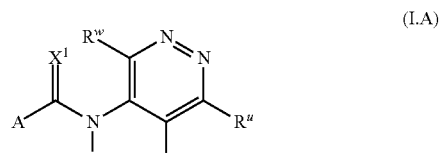

(I.A)

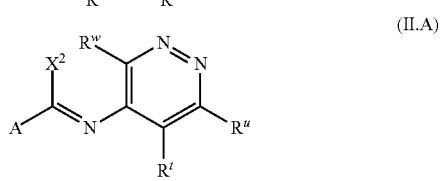

(II.A)

wherein A, $X^1$, $X^2$, $R^1$, $R^t$, $R^u$ and $R^w$ independently from each other are as defined herein.

Among the compounds of formulae I and II preference is further given to those compounds, wherein W is $CR^w$ with $R^w$ being hydrogen, i.e. W is CH and V is N.

Among the compounds of formulae I and II preference is further given to those compounds, wherein $R^t$, $R^u$, $R^v$ and $R^w$, if present, are selected independently of each other from hydrogen, fluorine, chlorine, bromine, methyl, difluoromethyl, trifluoromethyl, methoxy or difluoromethoxy with the proviso that if W is N, $R^v$ is hydrogen. More preferably, preference is given to those compounds, wherein at least two of the radicals $R^t$, $R^u$, $R^v$ or $R^w$, if present, are hydrogen.

One particular embodiment of the invention relates to compounds of formulae I or II, wherein V and W are selected from N and CH. Most particularly $R^t$, $R^u$, $R^v$ and $R^w$, if present, are hydrogen.

Another preferred embodiment of the invention relates to pyridazine compounds of formulae I and II, to the salts and N-oxides thereof and to the methods and uses of such compounds, wherein A is a radical A1.

Among the compounds, wherein A is A1, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A1, preference is given to those compounds, wherein $R^A$ is selected from hydrogen, halogen, CN, $NO_2$ $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^A$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably in the compounds wherein A is A1, $R^A$ is preferably selected from hydrogen, halogen, CN, $NO_2$, $C_1$-$C_4$-alkyl, $C_1$-$C_4$-haloalkyl, $C_3$-$C_6$-cycloalkyl $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^A$ is selected from hydrogen, halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl. In particular, $R^A$ is selected from hydrogen, halogen, $NO_2$, $C_1$-$C_4$-alkyl, $C_1$-$C_4$-haloalkyl, $C_3$-$C_6$-cycloalkyl and $C_3$-$C_6$-halocycloalkyl. More particularly $R^A$ is hydrogen, $C_1$-$C_2$-alkyl or $C_1$-$C_2$-haloalkyl.

Among the compounds of formulae I and II, wherein A is A1, preference is further given to those compounds, wherein $R^N$ if present is selected from $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from $OR^a$, $C(Y)R^b$, $C(Y)OR^c$, $S(O)_m R^d$, $NR^e R^f$, $C(Y)NR^g R^h$, $S(O)_m NR^e R^f$, $C(Y)NR^1 NR^e R^f$, $C_1$-$C_5$-alkylen-$OR^a$, $C_1$-$C_5$-alkylen-CN, $C_1$-$C_5$-alkylen-$C(Y)R^b$, $C_1$-$C_5$-alkylenC(Y)$OR^c$, $C_1$-$C_5$-alkylen-$NR^e R^f$, $C_1$-$C_5$-alkylen-$C(Y)NR^g R^h$, $C_1$-$C_5$-alkylen-$S(O)_m R^d$, $C_1$-$C_5$-alkylenS(O)$_m NR^e R^f$, $C_1$-$C_5$-alkylen-$NR^1 NR^e R^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents R.

Preferably in the compounds wherein A is A1, $R^N$ if present is preferably selected from $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from, heterocyclyl, hetaryl, $C_3$-$C_{10}$-cycloalkyl, $C_5$-$C_{10}$-cycloalkenyl, $C_1$-$C_4$-alkoxy-$C_2$-$C_4$-alkyl and heterocyclyl-$C_1$-$C_5$-alkyl, hetaryl-$C_1$-$C_5$-alkyl, $C_3$-$C_{10}$-cycloalkyl-$C_1$-$C_5$-alkyl and $C_5$-$C_{10}$-cycloalkenyl-$C_1$-$C_5$-alkyl.

Preferably in the compounds wherein A is A1, $R^N$ is preferably selected from $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and CN—$C_1$-$C_4$-alkyl.

In particular $R^N$ if present is $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy-$C_2$-$C_4$-alkyl. Further in particular, $R^N$ if present is $C_1$-$C_4$-alkyl, $C_1$-$C_4$-haloalkyl, $C_3$-$C_6$-cycloalkyl-$C_1$-$C_4$-alkyl. More preferably $R^N$ if present is $C_1$-$C_4$-alkyl or $C_1$-$C_4$-haloalkyl.

Examples of suitable radicals A1 are the radicals numbered A1.O1 to A1.O15 wherein Z is O and $R^A$ is represented by each line of the following Table A:

TABLE A

| No. | Z | $R^A$ |
|---|---|---|
| A1-O1 | O | H |
| A1-O2 | O | $CH_3$ |
| A1-O3 | O | $CH_2CH_3$ |
| A1-O4 | O | $CH_2CH_2CH_3$ |
| A1-O5 | O | c-Pr |
| A1-O6 | O | $CF_3$ |
| A1-O7 | O | $CHF_2$ |
| A1-O8 | O | $CHFCH_3$ |
| A1-O9 | O | $OCH_3$ |
| A1-O10 | O | $OCHF_2$ |
| A1-O11 | O | CN |
| A1-O12 | O | F |
| A1-O13 | O | Cl |
| A1-O14 | O | Br |
| A1-O15 | O | $NO_2$ |

Analog to the above listed radicals A1.O1 to A1.O15 are the radicals numbered A1.S1 to A1.S15 wherein Z instead of O is S and $R^A$ is represented by each line of the above Table A.

Analog to the above listed radicals A1.O1 to A1.O15 are the radicals numbered numbered A1.1N1 to A1.85N15 wherein Z instead of O is $NR^N$ with $R^N$ represented by each line of the following Table N and $R^A$ is represented by each line of the above Table A.

TABLE N

| No. | Radical $R^N$ |
|---|---|
| N-1 | H |
| N-2 | $CH_3$ |
| N-3 | $CH_2OCH_3$ |
| N-4 | $CH_2OCF_3$ |
| N-5 | $CH_2OCHF_2$ |
| N-6 | $CH_2OCH_2CH_3$ |
| N-7 | $CH_2CH_3$ |
| N-8 | $CH_2CH_2CH_3$ |
| N-9 | $CH(CH_2CH_2)$ |
| N-10 | $CH(CH_2CCl_2)$ |
| N-11 | $CH(CH_2CMe_2)$ |
| N-12 | $CH(CH_3)_2$ |
| N-13 | $CH_2CH(CH_2CH_2)$ |

TABLE N-continued

| No. | Radical $R^N$ |
|---|---|
| N-14 | $CH_2CH(CH_2CCl_2)$ |
| N-15 | $CH_2CH(CH_2CMe_2)$ |
| N-16 | $CH_2CF_3$ |
| N-17 | $CH_2CH_2CH_2CH_3$ |
| N-18 | $C(CH_3)_3$ |
| N-19 | $C_6H_5$ |
| N-20 | 4-Cl—$C_6H_4$ |
| N-21 | 4-F—$C_6H_4$ |
| N-22 | 2,4-$Cl_2$—$C_6H_3$ |
| N-23 | 4-($CH_3O$)—$C_6H_4$ |
| N-24 | 2-pyridyl |
| N-25 | 5-chloro-2-pyridyl |
| N-26 | $CH_2$—$C_6H_5$ |
| N-27 | 4-($F_3CO$)—$C_6H_4$ |
| N-28 | 4-($F_3CS$)—$C_6H_4$ |
| N-29 | 4-($F_2HCO$)—$C_6H_4$ |
| N-30 | 4-(($F_3C)_2FC$)—$C_6H_4$ |
| N-31 | 4-($SO_2CH_3$)—$C_6H_4$ |
| N-32 | 2,6-Cl-4-$CF_3$—$C_6H_2$ |
| N-33 | 3-Cl-5-$CF_3$-pyridine-2-yl |
| N-34 | 3-pyridyl |
| N-35 | 4-pyridyl |
| N-36 | 4-$NO_2$—$C_6H_4$ |
| N-37 | 4-$CF_3$—$C_6H_4$ |
| N-38 | 2,4-$F_2$—$C_6H_3$ |
| N-39 | 3,5-$Cl_2$—$C_6H_3$ |
| N-40 | 3,4-$Cl_2$—$C_6H_3$ |
| N-41 | 4-$C(CH_3)_3$—$C_6H_4$ |
| N-42 | 3-Cl—$C_6H_4$ |
| N-43 | 3-F—$C_6H_4$ |
| N-44 | 2-F—$C_6H_4$ |
| N-45 | 2-$CF_3$—$C_6H_4$ |
| N-46 | 2-$CH_3O$—$C_6H_4$ |
| N-47 | 3-$CH_3O$—$C_6H_4$ |
| N-48 | 3-Cl-4-F—$C_6H_3$ |
| N-49 | 3-$NO_2$—$C_6H_4$ |
| N-50 | 2-$CH_3$—$C_6H_4$ |
| N-51 | 3-$CH_3$—$C_6H_4$ |
| N-52 | 4-$CH_3$—$C_6H_4$ |
| N-53 | 2-F-4-Cl—$C_6H_3$ |
| N-54 | 2,4,6-$Cl_3$—$C_6H_2$ |
| N-55 | 2,3,4-$Cl_3$—$C_6H_2$ |
| N-56 | 2,6-$F_2$—$C_6H_3$ |
| N-57 | $CH_2F$ |
| N-58 | $CHF_2$ |
| N-59 | $CF_3$ |
| N-60 | $CH_2CHF_2$ |
| N-61 | $CH_2Cl$ |
| N-62 | $CHCl_2$ |
| N-63 | $CCl_3$ |
| N-64 | $CH_2CHCl_2$ |
| N-65 | $CH_2CCl_3$ |
| N-66 | $CH_2CH(CH_3)_2$ |
| N-67 | $CH_2CH_2OCH_3$ |
| N-68 | $CH_2CH_2OCF_3$ |
| N-69 | $CH_2CH_2OCHF_2$ |
| N-70 | $CH_2CH_2OCH_2CH_3$ |
| N-71 | 2-$NO_2$—$C_6H_4$ |
| N-72 | 6-Cl-2-pyridyl |
| N-73 | 5-$NO_2$-2-pyridyl |
| N-74 | 3-$NO_2$-2-pyridyl |
| N-75 | 6-$CH_3$-5-nitro-2-pyridyl |
| N-76 | vinyl |
| N-77 | 2-propenyl |
| N-78 | tetrahydrofuran-2-yl |
| N-79 | tetrahydrofuran-3-yl |
| N-80 | [1,3]dioxolan-2-yl |
| N-81 | [1,3]dioxolan-4-yl |
| N-82 | tetrahydrofuran-2-yl-methyl |
| N-83 | tetrahydrofuran-3-yl-methyl |
| N-84 | [1,3]dioxolan-2-yl-methyl |
| N-85 | [1,3]dioxolan-4-yl-methyl |

A further embodiment of the invention relates to pyridazine compounds of formulae I and II, to the salts and N-oxides thereof and to the methods and uses of such compounds, wherein A is a radical A2.

Among the compounds, wherein A is A2, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A2, preference is given to those compounds, wherein $R^A$ and $R^N$ have the same meaning as defined for the preferences in the above listed preferred compounds wherein A is a radical A1.

Examples of suitable radicals A2 are in analogy to the above listed radicals A1.O1 to A1.O15 the radicals A2 numbered A2.O1 to A2.O15 wherein Z is O and $R^A$ is represented by each line of the above Table A.

Further examples of radicals A2 are in analogy to the above listed radicals A1.S1 to A1.S15 the radicals A2 numbered A2.S1 to A2.S15 wherein Z is S and $R^A$ is represented by each line of the above Table A.

Further examples of radicals A2 are in analogy to the above listed radicals A1.1N1 to A1.85N15 the radicals A2 numbered A2.1N1 to A2.85N15 wherein Z is $NR^N$ with $R^N$ represented by each line of the above Table N and $R^A$ is represented by each line of the above Table A.

A further embodiment of the invention relates to pyridazine compounds of formulae I and II, to the salts and N-oxides thereof and to the methods and uses of such compounds, wherein A is a radical A3.

Among the compounds, wherein A is A3, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A3, preference is given to those compounds, wherein $R^A$ and $R^N$ have the same meaning as defined for the preferences in the above listed preferred compounds wherein A is a radical A1.

Examples of suitable radicals A3 are in analogy to the above listed radicals A1.O1 to A1.O15 the radicals A3 numbered A3.O1 to A3.O15 wherein Z is O and $R^A$ is represented by each line of the above Table A.

Further examples of radicals A3 are in analogy to the above listed radicals A1.S1 to A1.S15 the radicals A3 numbered A3.S1 to A3.S15 wherein Z is S and $R^A$ is represented by each line of the above Table A.

Further examples of radicals A3 are in analogy to the above listed radicals A1.1N1 to A1.85N15 the radicals A3 numbered A3.1N1 to A3.85N15 wherein Z is $NR^N$ with $R^N$ represented by each line of the above Table N and $R^A$ is represented by each line of the above Table A.

A further embodiment of the invention relates to pyridazine compounds of formulae I and II, to the salts and N-oxides thereof and to the methods and uses of such compounds, wherein A is a radical A4.

Among the compounds, wherein A is A4, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A4, preference is given to those compounds, wherein $R^A$ and $R^N$ have the same meaning as defined for the preferences in the above listed preferred compounds wherein A is a radical A1.

Examples of suitable radicals A4 are in analogy to the above listed radicals A1.O1 to A1.O15 the radicals A4 numbered A4.O1 to A4.O15 wherein Z is O and $R^A$ is represented by each line of the above Table A.

Further examples of radicals A4 are in analogy to the above listed radicals A1.S1 to A1.S15 the radicals A4 numbered A4.S1 to A4.S15 wherein Z is S and $R^A$ is represented by each line of the above Table A.

Further examples of radicals A4 are in analogy to the above listed radicals A1.1N1 to A1.85N15 the radicals A4 numbered A4.1N1 to A4.85N15 wherein Z is $NR^N$ with $R^N$ represented by each line of the above Table N and $R^A$ is represented by each line of the above Table A.

A further embodiment of the invention relates to pyridazine compounds of formulae I and II, to the salts and N-oxides thereof and to the methods and uses of such compounds, wherein A is a radical A5.

Among the compounds, wherein A is A5, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A5, preference is given to those compounds, wherein $R^A$ and $R^N$ have the same meaning as defined for the preferences in the above listed preferred compounds wherein A is a radical A1.

Examples of suitable radicals A5 are in analogy to the above listed radicals A1.O1 to A1.O15 the radicals A5 numbered A5.O1 to A5.O15 wherein Z is O and $R^A$ is represented by each line of the above Table A.

Further examples of radicals A5 are in analogy to the above listed radicals A1.S1 to A1.S15 the radicals A5 numbered A5.S1 to A5.S15 wherein Z is S and $R^A$ is represented by each line of the above Table A.

Further examples of radicals A5 are in analogy to the above listed radicals A1.1N1 to A1.85N15 the radicals A5 numbered A5.1N1 to A5.85N15 wherein Z is $NR^N$ with $R^N$ represented by each line of the above Table N and $R^A$ is represented by each line of the above Table A.

A further embodiment of the invention relates to pyridazine compounds of formulae I and II, to the salts and N-oxides thereof and to the methods and uses of such compounds, wherein A is a radical A6.

Among the compounds, wherein A is A6, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A6, preference is given to those compounds, wherein $R^A$ and $R^N$ have the same meaning as defined for the preferences in the above listed preferred compounds wherein A is a radical A1.

Examples of suitable radicals A6 are in analogy to the above listed radicals A1.O1 to A1.O15 the radicals A6 numbered A6.O1 to A6.O15 wherein Z is O and $R^A$ is represented by each line of the above Table A.

Further examples of radicals A6 are in analogy to the above listed radicals A1.S1 to A1.S15 the radicals A6 numbered A6.S1 to A6.S15 wherein Z is S and $R^A$ is represented by each line of the above Table A.

Further examples of radicals A6 are in analogy to the above listed radicals A1.1N1 to A1.85N15 the radicals A6 numbered A6.1N1 to A6.85N15 wherein Z is $NR^N$ with $R^N$ represented by each line of the above Table N and $R^A$ is represented by each line of the above Table A.

A very preferred embodiment of the invention relates to compounds of the formula I and to the salts and N-oxides thereof, wherein $X^1$ is O. These compounds are hereinafter also referred to as compounds I1.

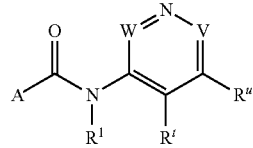

(I1)

In formula I1, the variables A, $R^1$, $R^t$, $R^u$, V and W are as defined herein.

Among the compounds of the formula I1, preference is given to those compounds, wherein at least one of the radicals $R^1$, $R^t$, $R^u$, V and W, preferably at least two of the radicals $R^1$, $R^t$, $R^u$, V and W, and more preferably all of the radicals $R^1$, $R^t$, $R^u$, V and W have one of the preferred meanings.

Preferred radicals $R^1$ of compounds as defined in the present invention are the radicals $R^1$ selected from hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1$-$C_5$-alkyl, $C_1$-$C_5$-alkylen-$OR^a$ and $C_3$-$C_{10}$-cycloalkyl-$C_1$-$C_5$-alkyl.

More preferred radicals $R^1$ of compounds as defined in the present invention are the radicals $R^1$ selected from hydrogen, $C_1$-$C_4$-alkyl, $C_1$-$C_4$-haloalkyl and $C_1$-$C_3$-alkylen-$OC_1$-$C_3$-alkyl.

Further more preferred radicals $R^1$ of compounds as defined in the present invention are the radicals $R^1$ selected from hydrogen and methyl.

Among the compounds of the formula I1, preference is further given to those compounds, wherein A is an oxadiazole radical, e.g.:
 a radical A1, selected from the oxadiazole radicals A1.O1 to A1.O15 or
 a radical A2, selected from the oxadiazole radicals A2.O1 to A2.O15 or
 a radical A3, selected from the oxadiazole radicals A3.O1 to A3.O15 or
 a radical A4, selected from the oxadiazole radicals A4.O1 to A4.O15 or
 a radical A5, selected from the oxadiazole radicals A5.O1 to A5.O15 or
 a radical A6, selected from the oxadiazole radicals A6.O1 to A6.O15.

Among the compounds of the formula I1, preference is further given to those compounds, wherein A is a thiadiazole radical, e.g.:
 a radical A1, selected from the thiadiazole radicals A1.S1 to A1.S15 or
 a radical A2, selected from the thiadiazole radicals A2.S1 to A2.S15 or
 a radical A3, selected from the thiadiazole radicals A3.S1 to A3.S15 or
 a radical A4, selected from the thiadiazole radicals A4.S1 to A4.S15 or
 a radical A5, selected from the thiadiazole radicals A5.S1 to A5.S15 or
 a radical A6, selected from the thiadiazole radicals A6.S1 to A6.S15.

Among the compounds of the formula I1, preference is further given to those compounds, wherein A is a triazole radical, e.g.:
 a radical A1, selected from the triazole radicals A1.1N1 to A1.85N15 or
 a radical A2, selected from the triazole radicals A2.1N1 to A2.85N15 or
 a radical A3, selected from the triazole radicals A3.1N1 to A3.85N15 or a radical A4, selected from the triazole radicals A4.1N1 to A4.85N15 or a radical A5, selected from the triazole radicals A5.1N1 to A5.85N15 or a radical A6, selected from the triazole radicals A6.1N1 to A6.85N15.

Particularly preferred embodiment of the invention relates to compounds of formula I1.A and to the salts and N-oxides thereof,

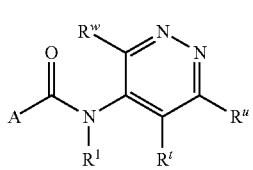

(I1.A)

wherein

A is a radical, as defined above for the preferred compounds of formula (II);

$R^1$ is hydrogen, $C_1$-$C_4$-alkyl, $C_1$-$C_4$-haloalkyl, $C_1$-$C_3$-alkylen-O—$C_1$-$C_3$-alkyl, most preferably hydrogen, methyl or ethyl;

$R^1$ is further most preferably represented by each individual line (1 to 77) of the Table B hereunder;

$R^t$, $R^u$, and $R^w$ are independently from each other selected from hydrogen, methyl, fluorine, chlorine, bromine, difluoromethyl, trifluoromethyl, methoxy and difluoromethoxy; and wherein preferably at least one, more preferably 2 or 3, of the radicals $R^t$, $R^u$, and $R^w$ are hydrogen.

TABLE B

| No. | $R^1$ |
|---|---|
| B-1 | Me |
| B-2 | $CH_2CH_3$ |
| B-3 | propyl |
| B-4 | iso-propyl |
| B-5 | butyl |
| B-6 | iso-butyl |
| B-7 | tert-butyl |
| B-8 | $CH_2C(CH_3)_3$ |
| B-9 | $CH_2CH=CH_2$ |
| B-10 | $CH_2CH=CCl_2$ |
| B-11 | $CH_2CH=CBr_2$ |
| B-12 | $CH_2CH_2F$ |
| B-13 | $CH_2CH_2Cl$ |
| B-14 | $CH_2CH_2Br$ |
| B-15 | $CH_2CHF_2$ |
| B-16 | $CH_2CHCl_2$ |
| B-17 | $CH_2CHBr_2$ |
| B-18 | $CH_2CF_3$ |
| B-19 | $CH_2CN$ |
| B-20 | $CH_2OCH_3$ |
| B-21 | $CH_2OCH_2CH_3$ |
| B-22 | $CH_2CH_2CN$ |
| B-23 | 2-cyanoethyl |
| B-24 | 2-methoxyethyl |
| B-25 | 2-ethoxyethyl |
| B-26 | cyclopropylmethyl |
| B-27 | cyclobutylmethyl |
| B-28 | cyclopentylmethyl |
| B-29 | oxetan-2-ylmethyl |
| B-30 | oxetan-3-ylmethyl |
| B-31 | oxolan-2-ylmethyl |
| B-32 | oxolan-3-ylmethyl |
| B-33 | thiethan-3-ylmethyl |
| B-34 | 1,1-dioxathiethan-3-ylmethyl |
| B-35 | cyclopropyl |
| B-36 | cyclobutyl |
| B-37 | cyclopentyl |

TABLE B-continued

| No. | $R^1$ |
|---|---|
| B-38 | oxetan-2-yl |
| B-39 | oxetan-3-yl |
| B-40 | oxolan-2-yl |
| B-41 | oxolan-3-yl |
| B-42 | thiethan-3-yl |
| B-43 | 1,1-dioxathiethan-3-yl |
| B-44 | benzyl |
| B-45 | 2-furylmethyl |
| B-46 | 3-furylmethyl |
| B-47 | 2-thienylmethyl |
| B-48 | 3-thienylmethyl |
| B-49 | isothiazol-3-ylmethyl |
| B-50 | isothiazol-4-ylmethyl |
| B-51 | isothiazol-5-ylmethyl |
| B-52 | isoxazol-3-ylmethyl |
| B-53 | oxazol-2-ylmethyl |
| B-54 | oxazol-5-ylmethyl |
| B-55 | oxazol-4-ylmethyl |
| B-56 | thiazol-2-ylmethyl |
| B-57 | thiazol-4-ylmethyl |
| B-58 | thiazol-5-ylmethyl |
| B-59 | 1H-pyrazol-3-ylmethyl |
| B-60 | 1H-pyrazol-4-ylmethyl |
| B-61 | 2H-pyrazol-3-ylmethyl |
| B-62 | 1-$CH_3$-1H-pyrazol-3-ylmethyl |
| B-63 | 1-$CH_3$-1H-pyrazol-4-ylmethyl |
| B-64 | 2-$CH_3$-2H-pyrazol-3-ylmethyl |
| B-65 | 1H-imidazol-2-ylmethyl |
| B-66 | 1H-imidazol-4-ylmethyl |
| B-67 | 1H-imidazol-5-ylmethyl |
| B-68 | 1-$CH_3$-1H-imidazol-2-ylmethyl |
| B-69 | 1-$CH_3$-1H-imidazol-4-ylmethyl |
| B-70 | 1-$CH_3$-1H-imidazol-5-ylmethyl |
| B-71 | oxazolin-2-ylmethyl |
| B-72 | thiazolin-2-ylmethyl |
| B-73 | 1H-imidazolin-2-ylmethyl |
| B-74 | 1-$CH_3$-1H-imidazolin-2-ylmethyl |
| B-75 | 1-phenylpyrazol-4-ylmethyl |
| B-76 | 5-methylfuran-2-ylmethyl |
| B-77 | 5,5-dimethyltetrahydrofuran-2-ylmethyl |

Particularly preferred embodiment of the invention relates to compounds of formula I1.A and to the salts and N-oxides thereof wherein A is a radical A1, wherein $R^A$ have the preferred meanings, in particular an oxadiazole radical of the formulae A1.O1 to A1.O15 wherein $R^1$, $R^t$, $R^u$ and $R^w$ are as defined above.

Examples of compounds of this particularly preferred embodiment are the compounds given in the following Table 1:

Table 1: Compounds of the formula I1.A, wherein $R^1$, $R^t$, $R^u$ and $R^w$ are hydrogen and wherein A is selected from the radicals A1.O1 to A1.O15.

Further examples of compounds of this particularly preferred embodiment are in analogy to the compounds listed in Table 1 the compounds wherein $R^1$ is a radical represented by each individual line (1 to 77) of the above Table B.

A particularly preferred embodiment of the invention relates to compounds of formula I1.A and to the salts and N-oxides thereof, wherein A is a radical A1, as defined herein, in particular a radical A1, wherein $R^A$ have the preferred meanings, in particular a thiadiazole radical of the formulae A1.S1 to A1.S15;

$R^1$, $R^t$, $R^u$, and $R^w$ are as defined above.

Examples of compounds of this particularly preferred embodiment are the compounds given in the following Table 2:

Table 2: Compounds of the formula I1.A, wherein $R^1$, $R^t$, $R^u$ and $R^w$ are hydrogen and wherein A is selected from the radicals A1.S1 to A1.S15.

Further examples of compounds of this particularly preferred embodiment are in analogy to the compounds listed in Table 2 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A1, as defined herein, in particular a radical A1, wherein $R^4$ have the preferred meanings, in particular a triazole radical of the formulae A1.1N1 to A1.85N15;
$R^1$, $R^t$, $R^u$, and $R^w$ are as defined above.

Examples of compounds of this particularly preferred embodiment are the compounds given in the following Table 3:

Table 3: Compounds of the formula I1.A wherein $R^1$, $R^t$, $R^u$ and $R^w$ are hydrogen and wherein A is selected from the radicals A1.1N1 to A1.85N15.

Further examples of compounds of this particularly preferred embodiment are in analogy to the compounds listed in Table 3 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A2, as defined herein, in particular a radical A2, wherein $R^4$ have the preferred meanings, in particular an oxadiazole radical of the formulae A2.O1 to A2.O15;
$R^1$, $R^t$, $R^u$, and $R^w$ are as defined above.

Examples of compounds of this particularly preferred embodiment are the compounds given in the following Table 4:

Table 4: Compounds of the formula I1.A wherein $R^1$, $R^t$, $R^u$ and $R^w$ are hydrogen and wherein A is selected from the radicals A2.O1 to A2.O15.

Further examples of compounds of this particularly preferred embodiment are in analogy to the compounds listed in Table 4 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A2, as defined herein, in particular a radical A2, wherein $R^4$ have the preferred meanings, in particular a thiadiazole radical of the formulae A2.S1 to A2.S15
$R^1$, $R^t$, $R^u$, and $R^w$ are as defined above.

Examples of compounds of this particularly preferred embodiment are the compounds given in the following Table 5:

Table 5: Compounds of the formula I1.A wherein $R^1$, $R^t$, $R^u$ and $R^w$ are hydrogen and wherein A is selected from the radicals A2.S1 to A2.S15.

Further examples of compounds of this particularly preferred embodiment are in analogy to the compounds listed in Table 5 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A2, as defined herein, in particular a radical A2, wherein $R^4$ have the preferred meanings, in particular a triazole radical of the formulae A1.1N1 to A1.85N15;
$R^1$, $R^t$, $R^u$, and $R^w$ are as defined above.

Examples of compounds of this particularly preferred embodiment are the compounds given in the following Table 6:

Table 6: Compounds of the formula I1.A wherein $R^1$, $R^t$, $R^u$ and $R^w$ are hydrogen and wherein A is selected from the radicals A2.1N1 to A2.85N15.

Further examples of compounds of this particularly preferred embodiment are in analogy to the compounds listed in Table 6 the compounds wherein $R^1$ is a radical represented by each individual line (1 to 77) of the above Table B.

A particularly preferred embodiment of the invention relates to compounds of formula I1.A and to the salts and N-oxides thereof, wherein A is a radical A3, as defined herein, in particular a radical A3, wherein $R^4$ have the preferred meanings, in particular an oxadiazole radical of the formulae A3.O1 to A3.O15;
$R^1$, $R^t$, $R^u$, and $R^w$ are as defined above.

Examples of compounds of this particularly preferred embodiment are the compounds given in the following Table 7:

Table 7: Compounds of the formula I1.A wherein $R^1$, $R^t$, $R^u$ and $R^w$ are hydrogen and wherein A is selected from the radicals A3.O1 to A3.O15.

Further examples of compounds of this particularly preferred embodiment are in analogy to the compounds listed in table 7 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A3, as defined herein, in particular a radical A3, wherein $R^4$ have the preferred meanings, in particular a thiadiazole radical of the formulae A3.S1 to A3.S15;
$R^1$, $R^t$, $R^u$, and $R^w$ are as defined above.

Examples of compounds of this particularly preferred embodiment are the compounds given in the following Table 8:

Table 8: Compounds of the formula I1.A wherein $R^1$, $R^t$, $R^u$ and $R^w$ are hydrogen and wherein A is selected from the radicals A3.S1 to A3.S15.

Further examples of compounds of this particularly preferred embodiment are in analogy to the compounds listed in Table 8 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A3, as defined herein, in particular a radical A3, wherein $R^4$ have the preferred meanings, in particular a triazole radical of the formulae A3.1N1 to A3.85N15;
$R^1$, $R^t$, $R^u$, and $R^w$ are as defined above.

Examples of compounds of this particularly preferred embodiment are the compounds given in the following Table 9:

Table 9: Compounds of the formula I1.A wherein $R^1$, $R^t$, $R^u$ and $R^w$ are hydrogen and wherein A is selected from the radicals A3.1N1 to A3.85N15.

Further examples of compounds of this particularly preferred embodiment are in analogy to the compounds listed in Table 9 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A4, as defined herein, in particular a radical A4, wherein $R^4$ have the preferred meanings, in particular an oxadiazole radical of the formulae A4.O1 to A4.O15;

$R^1$, $R^r$, $R^u$, and $R^w$ are as defined above.

Examples of compounds of this particularly preferred embodiment are the compounds given in the following Table 10:

Table 10: Compounds of the formula I1.A and the salts and N-oxides thereof, wherein $R^1$, $R^r$, $R^u$ and $R^w$ are hydrogen and wherein A is selected from the radicals A4.O1 to A4.O15.

Further examples of compounds of this particularly preferred embodiment are in analogy to the compounds listed in table 10 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A4, as defined herein, in particular a radical A4, wherein $R^4$ have the preferred meanings, in particular a thiadiazole radical of the formulae A4.S1 to A4.S15;

$R^1$, $R^r$, $R^u$, and $R^w$ are as defined above.

Examples of compounds of this particularly preferred embodiment are the compounds given in the following Table 11:

Table 11: Compounds of the formula I1.A, wherein $R^1$, $R^r$, $R^u$ and $R^w$ are hydrogen and wherein A is selected from the radicals A4.S1 to A4.S15.

Further examples of compounds of this particularly preferred embodiment are in analogy to the compounds listed in Table 11 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A4, as defined herein, in particular a radical A4, wherein $R^4$ have the preferred meanings, in particular a triazole radical of the formulae A4.1N1 to A4.85N15;

$R^1$, $R^r$, $R^u$, and $R^w$ are defined above.

Examples of compounds of this particularly preferred embodiment are the compounds given in the following Table 12:

Table 12: Compounds of the formula I1.A wherein $R^1$, $R^r$, $R^u$ and $R^w$ are hydrogen and wherein A is selected from the radicals A4.1N1 to A4.85N15.

Further examples of compounds of this particularly preferred embodiment are in analogy to the compounds listed in Table 12 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A5, as defined herein, in particular a radical A5, wherein $R^4$ have the preferred meanings, in particular an oxadiazole radical of the formulae A5.O1 to A5.O15;

$R^1$, $R^r$, $R^u$, and $R^w$ are as defined below.

Examples of compounds of this particularly preferred embodiment are the compounds given in the following Table 13:

Table 13: Compounds of the formula I1.A wherein $R^1$, $R^r$, $R^u$ and $R^w$ are hydrogen and wherein A is selected from the radicals A5.O1 to A5.O15

Further examples of compounds of this particularly preferred embodiment are in analogy to the compounds listed in Table 13 the compounds wherein $R^1$ is a radical represented by each individual line (1 to 77) of the above table B.

Particularly preferred embodiment of the invention relates to compounds of formula I1.A and to the salts and N-oxides thereof, wherein A is a radical A5, as defined herein, in particular a radical A5, wherein $R^4$ have the preferred meanings, in particular a thiadiazole radical of the formulae A5.S1 to A5.S15;

$R^1$, $R^r$, $R^u$, and $R^w$ are as defined above.

Examples of compounds of this particularly preferred embodiment are the compounds given in the following Table 14:

Table 14: Compounds of the formula I1.A wherein $R^1$, $R^r$, $R^u$ and $R^w$ are hydrogen and wherein A is selected from the radicals A5.S1 to A5.S15.

Further examples of compounds of this particularly preferred embodiment are in analogy to the compounds listed in table 14 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A5, as defined herein, in particular a radical A5, wherein $R^4$ have the preferred meanings, in particular a triazole radical of the formulae A5.1N1 to A5.85N15;

$R^1$, $R^r$, $R^u$, and $R^w$ are as defined above.

Examples of compounds of this particularly preferred embodiment are the compounds given in the following Table 15:

Table 15: Compounds of the formula I1.A wherein $R^1$, $R^r$, $R^u$ and $R^w$ are hydrogen and wherein A is selected from the radicals A5.1N1 to A5.85N15.

Further examples of compounds of this particularly preferred embodiment are in analogy to the compounds listed in Table 15 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A6, as defined herein, in particular a radical A6, wherein $R^4$ have the preferred meanings, in particular an oxadiazole radical of the formulae A6.O1 to A6.O15;

$R^1$, $R^r$, $R^u$, and $R^w$ are as defined above.

Examples of compounds of this particularly preferred embodiment are the compounds given in the following Table 16:

Table 16: Compounds of the formula I1.A wherein $R^1$, $R^r$, $R^u$ and $R^w$ are hydrogen and wherein A is selected from the radicals A6.O1 to A6.O15.

Further examples of compounds of this particularly preferred embodiment are in analogy to the compounds listed in Table 16 the compounds wherein $R^1$ is a radical represented by each individual line (1 to 77) of the above Table B.

Particularly preferred embodiment of the invention relates to compounds of formula I1.A and to the salts and N-oxides thereof, wherein A is a radical A6, as defined herein, in particular a radical A6, wherein $R^4$ have the preferred meanings, in particular a thiadiazole radical of the formulae A6.S1 to A6.S15;

$R^1$, $R^r$, $R^u$, and $R^w$ are as defined above.

Examples of compounds of this particularly preferred embodiment are the compounds given in the following Table 17:

Table 17: Compounds of the formula I1.A wherein $R^1$, $R^r$, $R^u$ and $R^w$ are hydrogen and wherein A is selected from the radicals A6.S1 to A6.S15.

Further examples of compounds of this particularly preferred embodiment are in analogy to the compounds listed in Table 17 the compounds wherein $R^1$ is a radical represented by each individual line (1 to 77) of the above table B.

Particularly preferred embodiment of the invention relates to compounds of formula I1.A and to the salts and N-oxides thereof, wherein A is a radical A6, as defined herein, in particular a radical A6, wherein $R^A$ have the preferred meanings, in particular a triazole radical of the formulae A6.1N1 to A6.85N15;

$R^1$, $R^t$, $R^u$, and $R^w$ are as defined above.

Examples of compounds of this particularly preferred embodiment are the compounds given in the following table 18:

Table 18: Compounds of the formula I1.A wherein $R^1$, $R^t$, $R^u$ and $R^w$ are hydrogen and wherein A is selected from the radicals A6.1N1 to A6.85N15.

Further examples of compounds of this particularly preferred embodiment are in analogy to the compounds listed in Table 18 the compounds wherein $R^1$ is a radical represented by each individual line (1 to 77) of the above Table B.

Another particularly preferred embodiment of the invention relates to compounds of formula I1.B and to the salts and N-oxides thereof, wherein

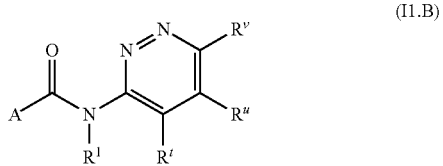

(I1.B)

A is a radical A1, as defined herein, in particular a radical A1, wherein $R^A$ has the preferred meanings, in particular an oxadiazole radical of the formulae A1.O1 to A1.O15;

$R^1$ is hydrogen, $C_1$-$C_4$-alkyl, $C_1$-$C_4$-haloalkyl, $C_1$-$C_3$-alkylen-O—$C_1$-$C_3$-alkyl, most preferably hydrogen, methyl or ethyl;

$R^1$ is further most preferably represented by a radical as defined in each line of Table B;

$R^t$, $R^u$ and $R^v$ are independently of each other selected from hydrogen, fluorine, chlorine, bromine, methyl, difluoromethyl, trifluoromethyl, methoxy and difluoromethoxy; and wherein preferably at least one, more preferably 2 or 3, of the radicals $R^t$, $R^u$, and $R^v$ are hydrogen.

Examples of compounds of this particularly preferred embodiment are the compounds given in the Table 19:

Tables 19: Compounds of the formula I1.B wherein $R^t$, $R^u$ and $R^v$ are hydrogen and wherein A and $R^1$ are as defined in Table 1.

An other particularly preferred embodiment of the invention relates to compounds of formula I1.B and to the salts and N-oxides thereof which are analogue to the compounds of formula I1.B wherein A is an oxadiazole radical A1 at the difference that A is an oxadiazole radical A2 and the remaining substituents have the same the definition.

An other particularly preferred embodiment of the invention relates to compounds of formula I1.B and to the salts and N-oxides thereof which are analogue to the compounds of formula I1.B wherein A is an oxadiazole radical A1 at the difference that A is an oxadiazole radical A3 and the remaining substituents have the same the definition.

An other particularly preferred embodiment of the invention relates to compounds of formula I1.B and to the salts and N-oxides thereof which are analogue to the compounds of formula I1.B wherein A is an oxadiazole radical A1 at the difference that A is an oxadiazole radical A4 and the remaining substituents have the same the definition.

An other particularly preferred embodiment of the invention relates to compounds of formula I1.B and to the salts and N-oxides thereof which are analogue to the compounds of formula I1.B wherein A is an oxadiazole radical A1 at the difference that A is an oxadiazole radical A5 and the remaining substituents have the same the definition.

An other particularly preferred embodiment of the invention relates to compounds of formula I1.B and to the salts and N-oxides thereof which are analogue to the compounds of formula I1.B wherein A is an oxadiazole radical A1 at the difference that A is an oxadiazole radical A6 and the remaining substituents have the same the definition.

Another particular preferred embodiment relates to compounds of the formula I1.B and to the salts and N-oxides thereof, wherein A is a radical A1, as defined herein, in particular a radical A1, wherein $R^A$ has the preferred meanings, in particular an thiadiazole radical of the formulae A1.S1 to A1.S15;

$R^1$ is hydrogen, $C_1$-$C_4$-alkyl, $C_1$-$C_4$-haloalkyl, $C_1$-$C_3$-alkylen-O—$C_1$-$C_3$-alkyl, most preferably hydrogen, methyl or ethyl;

$R^1$ is further most preferably represented by a radical as defined in each line of table B;

$R^t$, $R^u$ and $R^v$ are independently of each other selected from hydrogen, methyl, fluorine, chlorine, bromine, difluoromethyl, trifluoromethyl, methoxy and difluoromethoxy; and wherein preferably at least one, more preferably 2 or 3, of the radicals $R^t$, $R^u$, and $R^v$ are hydrogen.

Examples of compounds of this particularly preferred embodiment are the compounds given in the following Table 20.

Tables 20: Compounds of the formula I1.B wherein $R^t$, $R^u$ and $R^v$ are hydrogen and wherein A and $R^1$ are as defined in Table 2.

An other particularly preferred embodiment of the invention relates to compounds of formula I1.B and to the salts and N-oxides thereof which are analogue to the compounds of formula I1.B wherein A is a thiadiazole radical A1 at the difference that A is a thiadiazole radical A2 and the remaining substituents have the same the definition.

An other particularly preferred embodiment of the invention relates to compounds of formula I1.B and to the salts and N-oxides thereof which are analogue to the compounds of formula I1.B wherein A is a thiadiazole radical A1 at the difference that A is a thiadiazole radical A3 and the remaining substituents have the same the definition.

An other particularly preferred embodiment of the invention relates to compounds of formula I1.B and to the salts and N-oxides thereof which are analogue to the compounds of formula I1.B wherein A is a thiadiazole radical A1 at the difference that A is a thiadiazole radical A4 and the remaining substituents have the same the definition.

An other particularly preferred embodiment of the invention relates to compounds of formula I1.B and to the salts and N-oxides thereof which are analogue to the compounds of formula I1.B wherein A is a thiadiazole radical A1 at the difference that A is a thiadiazole radical A5 and the remaining substituents have the same the definition.

An other particularly preferred embodiment of the invention relates to compounds of formula I1.B and to the salts and N-oxides thereof which are analogue to the compounds of formula I1.B wherein A is a thiadiazole radical A1 at the difference that A is a thiadiazole radical A6 and the remaining substituents have the same the definition.

Another particular preferred embodiment relates to compounds of the formula I1.B and to the salts and N-oxides thereof, wherein A is a radical A1, as defined herein, in particular a radical A1, wherein $R^A$ has the preferred meanings, in particular a triazole radical of the formulae A1.1N1 to A1.85N15;

$R^1$ is hydrogen, $C_1$-$C_4$-alkyl, $C_1$-$C_4$-haloalkyl, $C_1$-$C_3$-alkylen-O—$C_1$-$C_3$-alkyl, most preferably hydrogen, methyl or ethyl;

$R^1$ is further most preferably represented by a radical as defined in each line of table B;

$R^t$, $R^u$ and $R^v$ are independently of each other selected from hydrogen, methyl, fluorine, chlorine, bromine, difluoromethyl, trifluoromethyl, methoxy and difluoromethoxy; and wherein preferably at least one, more preferably 2 or 3, of the radicals $R^t$, $R^u$, and $R^v$ are hydrogen.

Examples of compounds of this particularly preferred embodiment are the compounds given in the following Table 21.

Tables 21: Compounds of the formula I1.B wherein $R^t$, $R^u$ and $R^v$ are hydrogen and wherein A and $R^1$ are as defined in Table 3.

An other particularly preferred embodiment of the invention relates to compounds of formula I1.B and to the salts and N-oxides thereof which are analogue to the compounds of formula I1.B wherein A is a triazole radical A1 at the difference that A is a triazole radical A2 and the remaining substituents have the same the definition.

An other particularly preferred embodiment of the invention relates to compounds of formula I1.B and to the salts and N-oxides thereof which are analogue to the compounds of formula I1.B wherein A is a triazole radical A1 at the difference that A is a triazole radical A3 and the remaining substituents have the same the definition.

An other particularly preferred embodiment of the invention relates to compounds of formula I1.B and to the salts and N-oxides thereof which are analogue to the compounds of formula I1.B wherein A is a triazole radical A1 at the difference that A is a triazole radical A4 and the remaining substituents have the same the definition.

An other particularly preferred embodiment of the invention relates to compounds of formula I1.B and to the salts and N-oxides thereof which are analogue to the compounds of formula I1.B wherein A is a triazole radical A1 at the difference that A is a triazole radical A5 and the remaining substituents have the same the definition.

An other particularly preferred embodiment of the invention relates to compounds of formula I1.B and to the salts and N-oxides thereof which are analogue to the compounds of formula I1.B wherein A is a triazole radical A1 at the difference that A is a triazole radical A6 and the remaining substituents have the same the definition.

The compounds of the formula I, wherein $X^1$ is O (compounds I1), can be prepared e.g. according to the method depicted in scheme 1 by reacting an activated oxadiazole, thiadiazole or triazole carboxylic acid derivative II' with a 3- or 4-aminopyridazine, compound III (see e.g. Houben-Weyl: "Methoden der organ. Chemie" [Methods of Organic Chemistry], Georg-Thieme-Verlag, Stuttgart, New York 1985, Volume E5, pp. 941-1045). Activated oxadiazole, thiadiazole or triazole carboxylic acid derivatives II' are, for example, acyl halides, activated esters, anhydrides, acyl azides, wherein X is for example chlorine, fluorine, bromine, para-nitrophenoxy, pentafluorophenoxy, N-hydroxysuccinimides, hydroxybenzotriazol-1-yl. In scheme 1, the radicals A, $R^1$, $R^t$, $R^u$, V and W have the meanings mentioned above and in particular the meanings mentioned as being preferred.

Scheme 1:

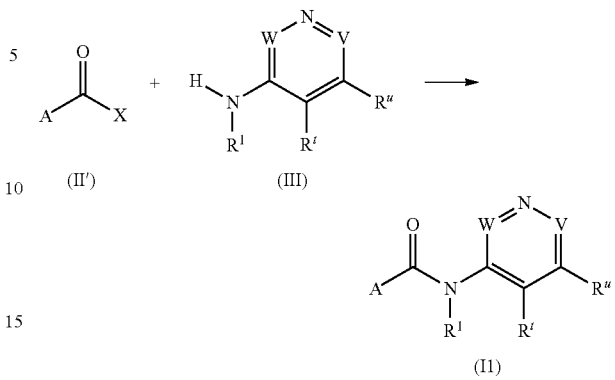

The compounds of the formula I, wherein $X^1$ is O (compounds I1), can also be prepared, for example, by reacting the oxadiazole, thiadiazole or triazole carboxylic acid IV and the 3- or 4-aminopyridazine compound III, in the presence of a coupling agent according to scheme 2. In scheme 2, the radicals A, $R^t$, $R^u$, V and W have the meaning given above and in particular the meanings given as being preferred.

Scheme 2:

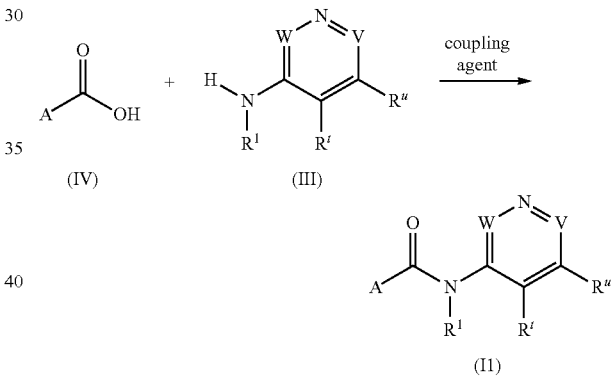

Suitable coupling agents are, for example: coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide; coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942]; coupling agents based on phosphonium salts, for example (benzotriazol-1-yloxy)tris(dimethylamino)phosphonium hexafluorophosphate [B. Castro, J. R. Domoy, G. Evin, C. Selye, Tetrahedron Lett. 1975, 14, 1219], (benzotriazol-1-yl-oxy)tripyrrolidinophosphonium hexafluorophosphate [J. Coste et al., Tetrahedron Lett. 1990, 31, 205]; coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647]; coupling agents which form acid chlorides, for example bis-(2-oxo-oxazolidinyl)phosphinic chloride [J. DiagoMesequer, Synthesis 1980, 547].

Compounds of formula I, wherein $X^1$ is O (compounds I1) and $R^1$ is different from hydrogen can also be prepared by alkylating the amides I (in which $R^1$ is hydrogen and which can be obtained according to scheme 1 or 2) using suitable alkylating agents in the presence of bases.

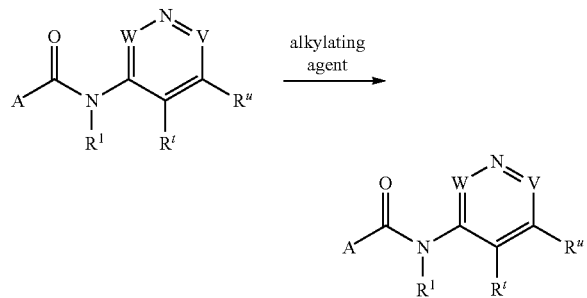

The oxadiazole, thiadiazole or triazole carboxylic acids IV and their activated derivatives II' as well as 3- or 4-aminopyridazine-compounds III are known in the art or are commercially available or can be prepared by methods known from the literature.

Compounds of the formula I, wherein $X^1$ is different from oxygen, can be prepared from the compounds of formula I' by standard methods:

Compounds of the formula I, wherein $X^1$ is S, can be prepared e.g. by reacting a compound of formula I1. with 2,4-bis(4-methoxyphenyl)-1,3,2,4-dithiadiphosphetane-2,4-disulfide or phorphorus pentasulfide according to the method described by M. Jesberger et al. in Synthesis 2003, 1929.

Compounds of the formula I, wherein $X^1$ is $NR^{1a}$, can be prepared e.g. by reacting a compound I1. with 2,4-bis(4-methoxyphenyl)-1,3,2,4-dithiadiphosphetane-2,4-disulfide to obtain the corresponding thioamide (compound I, wherein $X^1$ is S) which is then reacted with an appropriate amine according to the method described by V. Glushkov et al. in Pharmaceutical Chemistry Journal 2005, 39(10), 533-536.

Compounds of formula II, wherein $X^2=SR^{2a}$, can be prepared by alkylation of the corresponding thioamide (compound I, wherein $X^1$ is S) by reaction with an alkylating agent according to the method described by V. Glushkov et al. in Pharmaceutical Chemistry Journal 2005, 39(10), 533-536. Compounds I, wherein $X^2$ is $OR^{2a}$ or $NR^{2b}R^{2c}$, can be obtained in a similar manner. Compounds of the formula II, wherein $X^2=SOR^{2a}$ or $SO_2R^{2a}$ can be obtained by oxidation of compounds II with $X^2=SR^{2a}$.

N-oxides of the compounds of formulae I and II, can be prepared by oxidation of compounds I, according to standard methods of preparing heteroaromatic N-oxides, e.g. by the method described by C. Botteghi et al. in Journal of Organometallic Chemistry 1989, 370, 17-31.

As a rule, the compounds of formulae I or II can be prepared by the methods described above. If individual compounds can not be prepared via the above-described routes, they can be prepared by derivatization of other compounds I or II or by customary modifications of the synthesis routes described. For example, in individual cases, certain compounds I or II can advantageously be prepared from other compounds I or II by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the general formulae I or II may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formulae (I) or (II) or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formulae (I) or (II) or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects preferably insects of the order Homoptera.

The invention further provides an agricultural composition for combating such invertebrate pests, which comprises such an amount of at least one compound of the general formulae I or II or at least one agriculturally useful salt or N-oxide thereof and at least one inert liquid and/or solid agronomically acceptable carrier that has a pesticidal action and, if desired, at least one surfactant.

Such a composition may contain a single active compound of the formulae I or II or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formulae I or II and the pesticidical compositions comprising them are effective agents for controlling arthropod pests and nematodes. Invertebrate pests controlled by the compounds of formulae I or II include for example
insects from the order of the lepidopterans (Lepidoptera), for example *Agrotis ypsilon, Agrotis segetum, Alabama* argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani and Zeiraphera canadensis;

beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria;

dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa;

thrips (Thysanoptera), e.g. Dichromothrips corbetti, Frankliniella fusca, Frankliniella occidentalis, Frankliniella tritici, Scirtothrips citri, Thrips oryzae, Thrips palmi and Thrips tabaci;

hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta;

heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor;

homopterans (Homoptera), e.g. Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand, and Viteus vitifolii;

termites (Isoptera), e.g. Calotermes flavicollis, Leucotermes flavipes, Reticulitermes flavipes, Reticulitermes lucifugus and Termes natalensis;

orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

arachnoidea, such as arachnids (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis;

siphonatera, e.g. Xenopsylla cheopsis, Ceratophyllus spp.

The compositions and compounds of formulae I or II are useful for the control of nematodes, especially plant parasitic nematodes such as root knot nematodes, Meloidogyne hapla, Meloidogyne incognita, Meloidogyne javanica, and other Meloidogyne species;

cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Pin nematodes, Paratylenchus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

In a preferred embodiment of the invention the compounds of formulae I or II are used for controlling insects or arachnids, in particular insects of the orders Lepidoptera, Coleoptera, Thysanoptera and Homoptera and arachnids of the order Acarina. The compounds of the formulae I or II according to the present invention are particularly useful for controlling insects of the order Thysanoptera and Homoptera.

The compounds of formula formulae I or II or the pesticidal compositions comprising them may be used to protect growing plants and crops from attack or infestation by invertebrate pests, especially insects, acaridae or arachnids by contacting the plant/crop with a pesticidally effective amount of compounds of formulae I or II. The term "crop" refers both to growing and harvested crops.

The compounds of formulae I or II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols1, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formulae I or II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wetable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be Applied Undiluted for Foliar Applications. For Seed Treatment Purposes, such Products May be Applied to the Seed Diluted or Undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formulae I or II are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1 to 800 g/l of active ingredient, 1 to 200 g/l surfactant, 0 to 200 g/l antifreezing agent, 0 to 400 g/l of binder, 0 to 200 g/l of a pigment and up to 1 liter of a solvent, preferably water.

Other preferred FS formulations of compounds of formulae I or II for seed treatment comprise from 0.5 to 80% wt of the active ingredient, from 0.05 to 5% wt of a wetting agent, from 0.5 to 15% wt of a dispersing agent, from 0.1 to 5% wt of a thickener, from 5 to 20% wt of an anti-freeze agent, from 0.1 to 2% wt of an anti-foam agent, from 1 to 20% wt of a pigment and/or a dye, from 0 to 15% wt of a sticker/adhesion agent, from 0 to 75% wt of a filler/vehicle, and from 0.01 to 1% wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formulae I or II are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formulae I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formulae I or II as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulphoxide, aromatic hydrocarbons such as toluene, xylene, water, furthermore auxiliaries such as emulsifiers such as sorbitol monooleate, ° leyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, am-photeric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formulae I or II and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formulae I or II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formulae I and II or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formulae I or II into contact with each other, and "seed dressing" to methods of seed treatment which provide the seeds with an amount of the compounds of formulae I or II, i.e. which generate a seed comprising the compound of formulae I or II. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formulae I, or II or the enantiomers diastereomers or veterinarily acceptable salts thereof are in particular also suitable for being used for combating parasites in and on animals.

A further object of the present invention is therefore also to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formulae I or II or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of compounds of formulae I or II or the enantiomers or veterinarily acceptable salts thereof and an acceptable carrier or a composition comprising it.

The present invention also provides a non-therapeutic method for treating, controlling, preventing and protecting animals against infestation and infection by parasites, which comprises applying to a locus-P a parasiticidally effective amount of a compound of formulae I or II or the enantiomers or veterinarily acceptable salts thereof and an acceptable carrier or a composition comprising it.

The invention also provides a process for the preparation of a composition for treating, controlling, preventing or protecting animals against infestation or infection by parasites which comprises including a parasiticidally effective amount of a compound of formulae I or II or the enantiomers or veterinarily acceptable salts thereof and an acceptable carrier or a composition comprising it.

The invention relates further to the use of compounds of formula I for treating, controlling, preventing or protecting animals against infestation or infection by parasites.

The invention relates also to the use of a compound of formulae I or II or the enantiomers or veterinarily acceptable salts thereof and an acceptable carrier or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly, it has been found that compounds of formulae I or II are suitable for combating endo- and ectoparasites in and on animals. The compounds of formula I or II or the enantiomers or veterinarily acceptable salts thereof and compositions comprising them are suitable for systemic and/or non-systemic control of ecto- and/or endoparasites. They are active against all or some stages of development.

Compounds of formulae I or II or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formulae I or II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formulae I or II are especially useful for combating ectoparasites.

The compounds of formula I are especially useful for combating endoparasites.

The compounds of formulae I or II are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus,* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus, Anoplurida,* e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, *Strongylida,* e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi, Camallanida,* e.g. *Dracunculus medinensis* (guinea worm), *Spirurida,* e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formulae I or II and compositions containing them are particularly useful for the control of pests from the orders Diptera, Siphonaptera and Ixodida.

Moreover, the use of the formulae I or II and compositions containing them for combating mosquitoes is especially preferred.

The use of the compounds of formulae I or II and compositions containing them for combating flies is a further preferred embodiment of the present invention.

Furthermore, the use of the compounds of formulae I or II and compositions containing them for combating fleas is especially preferred.

The use of the compounds of formula formulae I or II and compositions containing them for combating ticks is a further preferred embodiment of the present invention.

The compounds of formulae I or II and compositions containing them also are especially useful for combating endoparasites (roundworms nematoda, thorny headed worms and planarians).

The compounds of formulae I or II and compositions containing them can be effective through both contact (via soil, glass, wall, bed net, carpet, blankets or animal parts) and ingestion (e.g. baits).

The present invention relates to the therapeutic and the non-therapeutic use of compounds of formulae I or II and compositions containing them for controlling and/or combating parasites in and/or on animals.

The compounds of formulae I or II and compositions containing them may be used to protect the animals from attack or infestation by parasites by contacting them with a parasitically effective amount of compounds of formulae I or II and compositions containing them.

As such, "contacting" includes both direct contact (applying the pesticidal mixtures/compositions containing the compounds of formula I or II according to the present invention directly on the parasite, which may include an indirect contact at it's locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of formula I.

"Locus-P" as defined above means the habitat, food supply, breeding ground, area, material or environment in which a parasite is growing or may grow outside of the animal. The compounds of the invention can also be applied preventively to places at which occurrence of the pests or parasites are expected.

The compounds of formula I can be effective through both contact (via soil, glass, wall, bed net, carpet, blankets or animal parts) and ingestion (e.g. baits).

Administration can be carried out prophylactically, therapeutically or nontherapeutically.

Administration of the active compounds is carried out directly or in the form of suitable preparations, orally, topically/dermally or parenterally.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally it is favorable to apply the compounds of formula I in total amounts of 0.5 mg/kg to 100 mg/kg per day, preferably 1 mg/kg to 50 mg/kg per day.

For oral administration to warm-blooded animals, the compounds of formula I or II may be formulated as animal feeds, animal feed premixes, animal feed concentrates, pills, solutions, pastes, suspensions, drenches, gels, tablets, boluses and capsules. In addition, the compounds of formulae I or II may be administered to the animals in their drinking water. For oral administration, the dosage form chosen should provide the animal with 0.01 mg/kg to 100 mg/kg of animal body weight per day of the formulae I or II compound, preferably with 0.5 mg/kg to 100 mg/kg of animal body weight per day.

Alternatively, the compounds of formulae I or II may be administered to animals parenterally, for example, by intraruminal, intramuscular, intravenous or subcutaneous injection. The compounds of formulae I or II may be dispersed or dissolved in a physiologically acceptable carrier for subcutaneous injection. Alternatively, the compounds of formulae I or II may be formulated into an implant for subcutaneous administration. In addition the compounds of formulae I or II may be transdermally administered to animals. For parenteral administration, the dosage form chosen should provide the animal with 0.01 mg/kg to 100 mg/kg of animal body weight per day of the compounds of formulae I or II.

The compounds of formulae I or II may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5 000 ppm and preferably 1 ppm to 3 000 ppm of the compounds of formulae I or II. In addition, the compounds of formulae I or II may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations; Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and accord ing to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointmentlike consistency results. The thickeners employed are the thickeners given above. Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are: water, alkanols, glycols, polyethylene glycols, polypropylene glycols, glycerol, aromatic alcohols such as benzyl alcohol, phenylethanol, phenoxyetha-nol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbon-ates such as propylene carbonate, ethylene carbonate, aromatic and/or aliphatic hydrocarbons, vegetable or synthetic oils, DMF, dimethylacetamide, N-alkylpyrrolidones such as N-Methylpyrrolidone, N-butylpyrrolidone or N-octylpyrrolidone, 2-pyrrolidone, 2,2-dimethyl-4-oxy-methylene-1,3-dioxolane and glycerol formal.

Suitable colorants are all colorants permitted for use on animals and which can be dis-solved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, cas-tor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids,
fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monoo-leate, sorbitan monostearate, glycerol monostearate, polyoxyethyl stearate, alkylphenol polyglycol ether; ampholytic surfactants such as di-sodium N-lauryl-piminodipropionate or lecithin; anionic surfactants, such as sodium lauryl sulfate, fatty alcohol ether sulfates, mono/dialkyl polyglycol ether orthophosphoric acid ester monoethanolamine salt;
cation-active surfactants, such as cetyltrimethylammonium chloride. Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formulae I or II.

Generally, it is favorable to apply the compounds of formulae I or II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formulae I or II against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formulae I or II are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formulae I or II in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formulae I or II. A detailed list of plastics and elastomers as well as preparation procedures for the shaped articles is given e.g. in WO 03/086075.

The active compounds can be applied solely or in a mixture with synergists or with other active compounds which act against pathogenic endo- and ectoparasites.

For example, the active compounds of formula I can be applied in mixtures with synthetic coccidiosis compounds, polyetherantibiotics as Amprolium, Robenidin, Toltrazuril, Monensin, Salinomycin, Maduramicin, Lasalocid, Narasin or Semduramicin or with other pesticides which are described in the list M below.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formulae I or II or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. R'anodine receptor modulators: flubendiamide and the phtalamid compound (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydroisoxazol-3-yl]-2-methyl-N-pyridin-2-ylmethyl-benzamide (M22.1), 4-[5-(3,5-Dichlorophenyl)-5-trifluoromethyl-4,5-dihydroisoxazol-3-yl]-2-methyl-N-(2,2,2-trifluoro-ethyl)benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4), 4-[5-(3,5-Dichlorophenyl)-5-[5-trifluoromethyl-4,5-dihydro-isoxazol-3-yl]-N-[(methoxyimino)methyl]-2-methylbenzamide (M22.5) 4-[5-(3-Chloro-5-trifluoromethyl-phenyl)-5-trifluoromethyl-4,5-dihydroisoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8); M.23. Anthranilamide compounds: chlorantraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile ($CF_2HCF_2CF_2CF_2CH_2C(CN)_2CH_2CH_2CF_3$) (M24.1) and 2-(2,2,3,3,4,4,5,5-octafluoropentyl)-2-(3,3,4,4,4-pentafluorobutyl)-malonodinitrile ($CF_2HCF_2CF_2$—$CF_2CH_2C(CN)_2CH_2CH_2CF_2CF_3$) (M24.2);

M.25. Microbial disruptors: *Bacillus thuringiensis* subsp. *lsraelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:

4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2 (5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R''cyclo-propanecarboxamide-2-(2,6-dichloro-α,α,α-trifluoro-p-tolyl)hydrazone or N—R'-2,2-di(R''') propionamide-2-(2,6-dichloro-α,α,α-trifluoro-p-tolyl)-hydrazone, wherein R' is methyl or ethyl, halo is chloro or bromo, R'' is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779.-AKD 1022 and its preparation have been described in U.S. Pat. No. 6,300,348.-M21.1 is known from WO 2007/101540. Isoxazolines M22.1 to M22.8 have been described in e.g. WO2005/085216, WO 2007/079162, WO 2007/026965, WO 2009/126668 and WO2009/051956. Anthranilamides M23.1 to M23.6 have been described in WO 2008/72743 and WO 200872783, those M23.7 to M23.12 in WO 2007/043677. Malononitriles M24.1 and M24.2 have been described in WO 02/089579, WO 02/090320, WO 02/090321, WO 04/006677, WO 05/068423, WO 05/068432 and WO 05/063694. Aminofuranones M26.1 to M6.10 have been described eg. in WO 2007/115644. Alkynylether M27.1 is described e.g. in JP 2006131529. Organic sulfur compounds have been described in WO 2007060839. Pyripyropene derivative M27.2 has been described in WO 2008/66153 and WO 2008/108491. Pyridazin M27.3 has been described in JP 2008/115155.

The following list of active substances, in conjunction with which the compounds according to the invention can be used, is intended to illustrate the possible combinations but does not limit them:

F.I) Respiration Inhibitors

F.I-1) Inhibitors of Complex III at Qo Site (e.g. Strobilurins)

strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)phenyl)-2-methoxyimino-N methyl-acetamide;

oxazolidinediones and imidazolinones: famoxadone, fenamidone;

F.I-2) Inhibitors of Complex II (e.g. Carboxamides):

carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of Complex III at Qi Site: Cyazofamid, Amisulbrom;

F.I-4) Other Respiration Inhibitors (Complex I, Uncouplers)

diflumetorim; tecnazen; ferimzone; ametoctradin; silthiofam;

nitrophenyl derivates: binapacryl, dinobuton, dinocap, fluazinam, nitrthal-isopropyl;

organometal compounds: fentin salts, such as fentin-acetate, fentin chloride or fentin hydroxide;

F.II) Sterol Biosynthesis Inhibitors (SBI Fungicides)

F.II-1) C14 demethylase inhibitors (DMI Fungicides, e.g. Triazoles, Imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine;

F.II-2) Delta14-Reductase Inhitors (Amines, e.g. Morpholines, Piperidines) morpholines: aldimorph, dodemorph, dodemorph-acetate, fenpropimorph, tridemorph; piperidines: fenpropidin, piperalin;

spiroketalamines: spiroxamine;

F.II-3) Inhibitors of 3-Keto Reductase: Hydroxyanilides: Fenhexamid;

F.III) Nucleic Acid Synthesis Inhibitors

F.III-1) RNA, DNA Synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA Topisomerase Inhibitors: Oxolinic Acid;

F.III-3) Nucleotide Metabolism (e.g. Adenosin-Deaminase)

hydroxy(2-amino)-pyrimidines: bupirimate;

F.IV) Inhibitors of Cell Division and or Cytoskeleton

F.IV-1) Tubulin Inhibitors: Benzimidazoles and Thiophanates: Benomyl, Carbendazim, fuberidazole, thiabendazole, thiophanate-methyl;

triazolopyrimidines: 5-chloro-7 (4-methylpiperidin-1-yl)-6-(2,4,6-trifluorophenyl)-[1,2,4]triazolo[1,5a]pyrimidine F.IV-2) Other Cell Division Inhibitors benzamides and phenyl acetamides: diethofencarb, ethaboxam, pencycuron, fluopicolide, zoxamide;

F.IV-3) Actin Inhibitors: Benzophenones: Metrafenone;

F.V) Inhibitors of Amino Acid and Protein Synthesis

F.V-1) Mmethionine Synthesis Inhibitors (Anilino-Pyrimidines)

anilino-pyrimidines: cyprodinil, mepanipyrim, nitrapyrin, pyrimethanil;

F.V-2) Protein Synthesis Inhibitors (Anilino-Pyrimidines)

antibiotics: blasticidin-S, kasugamycin, kasugamycin hydrochloride-hydrate, mildiomycin, streptomycin, oxytetracyclin, polyoxine, validamycin A;

F.VI) Signal Transduction Inhibitors

F.VI-1) MAP/Histidine Kinase Inhibitors (e.g. Anilino-Pyrimidines)

dicarboximides: fluoroimid, iprodione, procymidone, vinclozolin;

phenylpyrroles: fenpiclonil, fludioxonil;

F.VI-2) G Protein Inhibitors: Quinolines: Quinoxyfen;

F.VII) Lipid and Membrane Synthesis Inhibitors

F.VII-1) Phospholipid Biosynthesis Inhibitors organophosphorus compounds: edifenphos, iprobenfos, pyrazophos;

dithiolanes: isoprothiolane;

F.VII-2) Lipid Peroxidation aromatic hydrocarbons: dicloran, quintozene, tecnazene, tolclofos-methyl, biphenyl, chloroneb, etridiazole;

F.VII-3) carboxyl acid amides (CAA fungicides)

cinnamic or mandelic acid amides: dimethomorph, flumorph, mandipromaid, pyrimorph;

valinamide carbamates: benthiavalicarb, iprovalicarb, pyribencarb, valifenalate and N-(1-(1-(4-cyano-phenyl) ethanesulfonyl)-but-2-yl)carbamic acid-(4-fluorophenyl) ester;

F.VII-4) Compounds Affecting Cell Membrane Permeability and Fatty Acides carbamates: propamocarb, propamocarb-hydrochlorid F.VIII) Inhibitors with Multi Site Action F.VIII-1) Inorganic Active Substances: Bordeaux Mixture, Copper Acetate, Copper Hydroxide, Copper Oxychloride, Basic Copper Sulfate, Sulfur;

F.VIII-2) Thio- and Dithiocarbamates: Ferbam, Mancozeb, Maneb, Metam, Methasulphocarb, metiram, propineb, thiram, zineb, ziram;

F.VIII-3) Organochlorine Compounds (e.g. Phthalimides, Sulfamides, Chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: Guanidine, Dodine, Dodine Free Base, Guazatine, Guazatineacetate, Iminoctadine, Iminoctadine-Triacetate, Iminoctadine-Tris(Albesilate);

F.VIII-5) Ahtraquinones: Dithianon;

F.IX) Cell Wall Synthesis Inhibitors

F.IX-1) Inhibitors of Glucan Synthesis: Validamycin, Polyoxin B;

F.IX-2) Melanin Synthesis Inhibitors: Pyroquilon, Tricyclazole, Carpropamide, Dicyclomet, fenoxanil;

F.X) Plant Defence Inducers

F.X-1) Salicylic Acid Pathway: Acibenzolar-S-Methyl;

F.X-2) Others: Probenazole, Isotianil, Tiadinil, Prohexadione-Calcium;

phosphonates: fosetyl, fosetyl-aluminum, phosphorous acid and its salts;

F.XI) Unknown Mode of Action: bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propyl-chromen-4-one, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazol-1-yl)-acetyl]-piperidin-4-yl}-thiazole-4-carboxylic acid methyl(1,2,3,4-tetrahydronaphthalen-1-yl)-amide, 2-{1-[2-(5-methyl-3-trifluoromethyl-pyrazol-1-yl)-acetyl]-piperidin-4-yl}-thiazole-4-carboxylic acid methyl-(R)-1,2,3,4-tetrahydronaphthalen-1-yl-amide, methoxyacetic acid 6-tert-butyl-8-fluoro-2,3-dimethylquinolin-4-yl ester and N-Methyl-2-{1-[(5-methyl-3-trifluoromethyl-1H-pyrazol-1-yl)acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydropyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)isoxazol-5-yl]-2-prop-2-ynyloxy-acetamide;

F.XI) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri-iodobenzoic acid, trinexapac-ethyl and uniconazole;

F.XII) Biological control agents: antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), Ulocladium oudemansii (e.g. the product BOTRY-ZEN from BotriZen Ltd., New Zealand), Chitosan (e.g. ARMOUR-ZEN from BotriZen Ltd., New Zealand).

The invertebrate pest, i.e. arthropodes and nematodes, the plant, soil or water in which the plant is growing can be contacted with the compound(s) of formulae I or II or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formulae I or II. As such, the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formulae I or II and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formulae I and II can also be applied preventively to places at which occurrence of the pests is expected.

The compounds of formulae I or II may also be used to protect growing plants from attack or infestation by pests by contacting the plant with a pesticidally effective amount of compounds of formula I or II. As such, "contacting the plant" includes both direct contact (applying the compounds/compositions directly on the pest and/or plant-typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 10 g to 150 g per 100 kg of seed.

The present invention is now illustrated in further detail by the following examples:

I. Preparation Examples

The procedures described in the following preparation examples were used to prepare further compounds of formulae I and II by appropriate modification of the starting material. The resulting compounds, together with physical data, are listed in the table C below.

Products may be characterized by H PLC-MS (High Performance Liquid Chromatography Mass Spectrometry). HPLC was carried out using an analytic RP-18 column (Chromolith Speed ROD from Merck KgaA, Germany) which was operated at 40° C. Acetonitrile with 0.1% by volume of a trifluoroacetic acid/water mixture and 0.1% by volume of trifluoroacetic acid served as mobile phase; flow rate: 1.8 ml/min and injection volume: 2 μl.

1-(2-Methoxyethyl)-N,5-dimethyl-N-pyridazin-4-yltriazole-4-carboxamide (example III.7)

O-(7-Azabenzotriazol-1-yl)-N,N,N',N'-tetramethyluronium hexafluorophosphat (HATU; 1.23 g, 3.24 mmol, 3.00 eq) and N-methylmorpholine (0.71 ml, 0.66 g, 6.5 mmol, 6.0 eq) was added to a solution of 1-(2-methoxyethyl)-5-methyl-triazole-4-carboxylic acid (200 mg, 1.08 mmol) and N-methylpyridazin-4-amine (118 mg, 1.08 mmol, 1.00 eq) in DMF (2.5 ml) and the mixture was stirred at room temperature for 4 d. After removal of the solvent, the residue was dissolved in dichloromethane, washed twice with sat. aq. NaHCO$_3$ sol. and once with brine and dried over Na$_2$SO$_4$. Removal of the solvent under vacuum and chromatographic purification (CH:EtOAc) gave the title compound as a brown oil (200 mg, 64%, 95% purity).

HPLC/MS: r.t. 1.406 min, m/z [MH]$^+$ 277.1

Compounds wherein A is A1

| No. | Z | R$^1$ | R$^A$ | r.t. [min][a] | m/z[b] |
|---|---|---|---|---|---|
| I.1 | N—CH$_2$CF$_3$ | H | CH$_3$ | 2.050 | 287.1 |
| I.2 | N—CH$_2$CF$_3$ | CH$_3$ | CH$_3$ | 1.997 | 301.1 |

Compounds wherein A is A2

| No. | Z | R$^1$ | R$^A$ | r.t. [min][a] | m/z[b] |
|---|---|---|---|---|---|
| II.1 | S | H | H | 1.206 | 208.0 |
| II.2 | S | CH$_3$ | H | 1.072 | 222.0 |
| II.3 | N—CH$_2$CH$_2$OCH$_3$ | H | CH$_3$ | 1.352 | 263.1 |
| II.4 | N—CH$_2$cPr | H | CH$_3$ | 1.740 | 259.1 |
| II.5 | N—iBu | H | CH$_3$ | 1.874 | 261.1 |
| II.6 | N—CH$_2$CH$_2$OCH$_3$ | CH$_3$ | CH$_3$ | 1.442 | 277.1 |
| II.7 | N—CH$_2$cPr | CH$_3$ | CH$_3$ | 1.775 | 273.1 |
| II.8 | N—iBu | CH$_3$ | CH$_3$ | 1.939 | 275.2 |
| II.9 | N—CH$_2$CF$_3$ | H | CH$_3$ | 1.728 | 287.1 |
| II.10 | N—CH$_2$CF$_3$ | CH$_3$ | CH$_3$ | 1.804 | 301.1 |

Compounds wherein A is A3

| No. | Z | R$^1$ | R$^A$ | r.t. [min][a] | m/z[b] |
|---|---|---|---|---|---|
| III.1 | S | H | H | 1.017 | 208.0 |
| III.2 | S | CH$_3$ | H | 1.086 | 222.0 |
| III.3 | N—CH$_2$CH$_2$OCH$_3$ | H | CH$_3$ | 1.488 | 263.1 |
| III.4 | N—CH$_2$cPr | H | CH$_3$ | 1.878 | 259.1 |
| III.5 | N—iBu | H | CH$_3$ | 2.030 | 261.1 |
| III.6 | N—CH$_2$CF$_3$ | H | CH$_3$ | 1.800 | 287.1 |
| III.7 | N—CH$_2$CH$_2$OCH$_3$ | CH$_3$ | CH$_3$ | 1.406 | 277.1 |
| III.8 | N—CH$_2$cPr | CH$_3$ | CH$_3$ | 1.762 | 273.1 |
| III.9 | N—iBu | CH$_3$ | CH$_3$ | 1.943 | 275.2 |
| III.10 | N—CH$_2$CF$_3$ | CH$_3$ | CH$_3$ | 1.748 | 301.1 |
| III.11 | N-2-Cl-3-pyridyl | H | CH$_3$ | 1.798 | 316.1 |
| III.12 | N-2-Cl-3-pyridyl | CH$_3$ | CH$_3$ | 1.772 | 330.1 |
| III.13 | N-2-Cl-3-pyridyl | CH$_2$OCH$_3$ | CH$_3$ | 1.972 | 360.1 |

[a] retention time HPLC/MS
[b] [M + H]+ peaks HPLC/MS

II. Evaluation of Pesticidal Activity

II.1 Cowpea Aphid (*Aphis craccivora*)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assessed after 24, 72, and 120 hours.

In this test, the compounds I.1, II.1, II.8, II.9, III.1, III.3, III.4, III.5, III.6, III.7, III.8 and III.10 at 500 ppm showed a mortality of at least 75% in comparison with untreated controls.

II.2 Cotton aphid (*Aphis gossypii*, Mixed Life Stages)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds I.1, II.8, II.9, III.6, III.7, III.8 and III.9 at 500 ppm showed a mortality of at least 75% in comparison with untreated controls.

II.3 Vetch aphid (*Megoura viciae*)

The active compounds were formulated in 1:3 (vol:vol) DMSO: water with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiter plates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds III.3, III.5 and III.10 at a concentration of the test solution of 2500 mg/l showed a mortality of at least 75%.

II.4 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds II.9, III.1, III.3, III.4, III.5, III.6, III.8, III.9 and III.10 at 2500 ppm showed at least 75% mortality in comparison with untreated controls.

The invention claimed is:
1. A compound of formula (I) or (II),

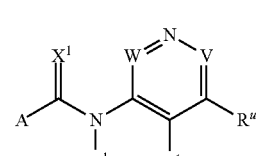

(I)

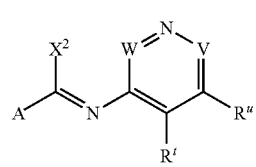

(II)

wherein

A is a triazole, a thiadiazole, or an oxadiazole radical of formulae A1, A2, A3, A4, A5 or A6

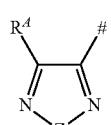

A1

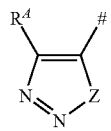

A2

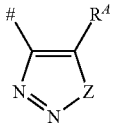

A3

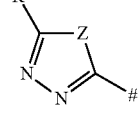

A4

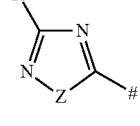

A5

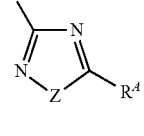

A6 wherein

\# denotes the binding site to the remainder of formulae I or II, and wherein $R^A$ is independently of each other selected from the group consisting of hydrogen, halogen, CN, $NO_2$, $C_1$-$C_{10}$-alkyl, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein each $R^A$ is further independently of each other selected from the group consisting of $OR^a$, $C(Y)R^b$, $C(Y)OR^c$, $S(O)_mR^d$, $NR^eR^f$, heterocyclyl, $C_3$-$C_{10}$-cycloalkyl and $C_5$-$C_{10}$-cycloalkenyl, wherein the last three mentioned radicals may be unsubstituted or may carry 1, 2, 3, 4 or 5 identical or different substituents $R^x$, wherein Z is O, S or $NR^N$ V is $C(R^v)$ or N;

W is $C(R^w)$ or N;

with the proviso that either V or W is N;

$R^N$ is selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from the group consisting of $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^1NR^eR^f$, $C_1$-$C_5$-alkylen-$OR^a$, $C_1$-$C_5$-alkylen-CN, $C_1$-$C_5$-alkylen-C$(Y)R^b$, $C_1$-$C_5$-alkylen-C(Y)$OR^c$, $C_1$-$C_5$-alkylen-$NR^eR^f$, $C_1$-$C_5$-alkylen-C(Y)$NR^gR^h$, $C_1$-$C_5$-alkylen-S$(O)_m$ $R^d$, $C_1$-$C_5$-alkylen-S$(O)_mNR^eR^f$, $C_1$-$C_5$-alkylen-$NR^1NR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents $R^y$ $R^t$, $R^u$, $R^v$ and $R^w$ are independently of each other selected from the group consisting of hydrogen, halogen, $C_1$-$C_3$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

$X^1$ is S, O or $NR^{1a}$, wherein $R^{1a}$ is selected from the group consisting of hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, heterocyclyl, phenyl-$C_1$-$C_4$-alkyl, hetaryl-$C_1$-$C_4$-alkyl, and heterocyclyl-$C_1$-$C_4$-alkyl wherein the ring in the six last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^2$ is $OR^{2a}$, $NR^{2b}R^{2c}$, $S(O)_mR^{2d}$, wherein $R^{2a}$ is selected from the group consisting of $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2b}$, $R^{2c}$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or $R^{2b}$ and $R^{2c}$ together with the nitrogen atom to which they are bound form a 5- or 6-membered, saturated or unsaturated heterocycle, which may carry a further heteroatom being selected from the group consisting of O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2d}$ is selected from the group consisting of $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^1$ is hydrogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $OR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, phenyl, hetaryl, heterocyclyl, $C_1$-$C_5$-alkylen-$OR^a$, $C_1$-$C_5$-alkylen-CN, phenyl-$C_1$-$C_5$-alkyl, hetaryl-$C_1$-$C_5$-alkyl, heterocyclyl-$C_1$-$C_5$-alkyl, $C_3$-$C_{10}$-cycloalkyl-$C_1$-$C_5$-alkyl, $C_1$-$C_5$-alkylen-C$(Y)R^b$, —$C_1$-$C_5$-alkylen-C(Y)$OR^c$, $C_1$-$C_5$-alkylen-$NR^eR^f$, $C_1$-$C_5$-alkylen-C(Y)$NR^gR^h$, $C_1$-$C_5$-alkylen-S$(O)_2R^d$, $C_1$-$C_5$-alkylen-S$(O)_mNR^eR^d$, or $C_1$-$C_5$-alkylen-C(Y)$NR^1NR^eR^f$ wherein the last sixteen mentioned radicals may be unsubstituted or may carry 1, 2, 3, 4 or 5 identical or different substituents $R^x$ or $R^y$;

m is 0, 1 or 2

Y is O or S;

$R^a$, $R^b$, $R^c$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from the group consisting of $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from the group consisting of O, S and N as a ring member atom and wherein the heterocycle may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^i$ is selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from the group consisting of cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals $R^y$; and wherein $R^y$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$ haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

or its agriculturally or veterinally acceptable salt, N-oxide, enantiomer, or diastereomer thereof.

2. The compound as claimed in claim 1, wherein the pyridazine compound is a compound of formula (I).

3. The compound as claimed in claim 2, wherein $X^1$ is oxygen.

4. The compound as claimed in claim 2, wherein $R^1$ is hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1$-$C_5$-alkyl, $C_1$-$C_5$-alkylen-$OR^a$, or $C_3$-$C_{10}$-cycloalkyl-$C_1$-$C_5$-alkyl.

5. The compound as claimed in claim 2, wherein $R^1$ is hydrogen, $C_1$-$C_4$-alkyl, $C_1$-$C_4$-haloalkyl or $C_1$-$C_3$-alkylen-O—$C_1$-$C_3$-alkyl.

6. The compound as claimed in claim 1, wherein W is $CR^w$ with $R^w$ being hydrogen.

7. The compound as claimed in claim 1, wherein $R^t$, $R^u$, $R^v$ and $R^w$, if present, are selected independently of each other from the group consisting of hydrogen, fluorine, chlorine, bromine, methyl, difluoromethyl, trifluoromethyl, methoxy and difluoromethoxy.

8. The compound as claimed in claim 1, wherein the radicals $R^t$, $R^u$, $R^w$ are hydrogen.

9. The compound as claimed in claim 1, wherein A is A1.

10. The compound as claimed in claim 1, wherein A is A2 or A3.

11. The compound as claimed in claim 1, wherein A is A4.

12. The compound as claimed in claim 1, wherein A is A5 or A6.

13. The compound as claimed in claim 1 wherein if present, $R^N$ is selected from the group consisting of $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and CN—$C_1$-$C_4$-alkyl.

14. The compound as claimed in claim 1, wherein $R^4$ is selected from the group consisting of hydrogen, halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl.

15. A method for controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a compound of claim 1.

16. The method as claimed in claim 15, wherein the invertebrate pests are arthropod pests and/or nematodes.

17. The method as claimed in claim 16, wherein the invertebrate pests are insects of the order Homoptera.

18. A method for protecting plant propagation material and/or the plants which grow therfrom, which method comprises treating the plant propagation material with a pesticidally effective amount of a compound claim 1.

19. Plant propagation material treated with at least one compound of claim 1.

* * * * *